(12) United States Patent
Cashman

(10) Patent No.: US 7,763,710 B2
(45) Date of Patent: Jul. 27, 2010

(54) ALS-SPECIFIC PEPTIDE COMPOSITION

(75) Inventor: Neil Cashman, Vancouver (CA)

(73) Assignee: Amorfix Life Sciences Ltd., Mississauga, Ontario (CA)

( * ) Notice: Subject to any disclaimer, the term of this patent is extended or adjusted under 35 U.S.C. 154(b) by 0 days.

(21) Appl. No.: 12/236,731

(22) Filed: Sep. 24, 2008

(65) Prior Publication Data

US 2009/0098151 A1  Apr. 16, 2009

Related U.S. Application Data

(60) Division of application No. 11/367,609, filed on Mar. 3, 2006, now Pat. No. 7,439,324, which is a continuation-in-part of application No. PCT/CA2004/001503, filed on Aug. 20, 2004.

(60) Provisional application No. 60/496,381, filed on Aug. 20, 2003, provisional application No. 60/497,362, filed on Aug. 21, 2003.

(51) Int. Cl.
C07K 5/00 (2006.01)
C07K 16/00 (2006.01)

(52) U.S. Cl. .................... 530/327; 530/387.1

(58) Field of Classification Search .............. None
See application file for complete search history.

(56) References Cited

U.S. PATENT DOCUMENTS

| 6,406,864 | B2 | 6/2002 | Prusiner et al. |
| 6,677,125 | B2 | 1/2004 | Prusiner et al. |
| 7,041,807 | B1 | 5/2006 | Prusiner et al. |
| 7,439,324 | B2 | 10/2008 | Cashman |
| 2002/0123072 | A1 | 9/2002 | Prusiner et al. |
| 2007/0003977 | A1 | 1/2007 | Cashman et al. |

FOREIGN PATENT DOCUMENTS

CA  2408762  4/2003
CA  2452946  6/2004

OTHER PUBLICATIONS

Pardo, C. et al., Superoxide dismutase is an abundant component in cell bodies, dendrites, and axons of motor neurons and in a subset of other neurons, Proc. Natl. Acad. Sci. USA, vol. 92, pp. 954-958 (Feb. 14, 1995) (Neurobiology).
Lehto, M.T., et al, Society for Neurscience Annual Meeting; Nov. 2-7. 2002; Peroxynitrite as a Probe for the Structure of Normal and Misfolded Prion Protein, Program No. 692.9, Poster.
Lehto, M.T. et al., Society for Neuroscience Annual Meeting; Aug. 21, 2002, Peroxynitrite as a Probe for the Structure of Normal and Misfolded Prion Protein, PRP, Program No. 692.9, Abstract.
Bolton, et al. (Jul. 1991), Molecular location of a species-specific epitope on the hampster scrapie agent protein, J. of Virology, 65(7):3667-3675.
Safer et al. (Nov. 2002), Measuring Prions causing bovine spongiform encephalopathy or chronic wasting disease by immunoassays and transgenic mice, Nat. Biotechnol, 20(11):1147-1150.
Paramithiotis et al. (Jul. 2003), A prion protein epitope selective for the pathologically misfolded conformation, Nat. Med., 9(7):893-899.
Soto C. (Oct. 2004), Diagnosing prion diseases; needs, challenges and hopes, Nature Rev. Microbiol, 2 (10):809-819.
Product No. S-2147 Product Information Sheet [online] Aug. 1996. [Retreived on Oct. 23, 2007]. Retreived from http://www.sigmaaldrich.com/sigma/datasheet/s2147-066h4833.pdf.
UniProtKB/Swiss-Prot entry P00441, SODC_HUMAN, Jul. 21, 1986.
Harris et al. Micron, 30:597-623 Dec. 1999.
Kim et al. Free Rad. Biol. Med. 2002. 32:544-550.
Burgess et al. J of. Cell Biol. 1990. 111:2129-2138.
Bowie et al. Science, 1990, 247:1306-1310.
Pawson et al. 2003, Science 300:445-452.
Johnston et al., PNAS, 97(23):12571-12576, Nov. 2000.
Kunst et al., Nature Genetics, 15:91-94, 1997.

*Primary Examiner*—John D Ulm
*Assistant Examiner*—Stacey MacFarlane
(74) *Attorney, Agent, or Firm*—Bereskin & Parr LLP; Noel Courage; Carmela DeLuca

(57) ABSTRACT

The invention relates to a composition for eliciting an immune response in an animal to produce an antibody that binds selectively to an amyotrophic lateral sclerosis (ALS)-specific epitope.

4 Claims, 9 Drawing Sheets

A

FIGURE 4 – CONTINUED
B
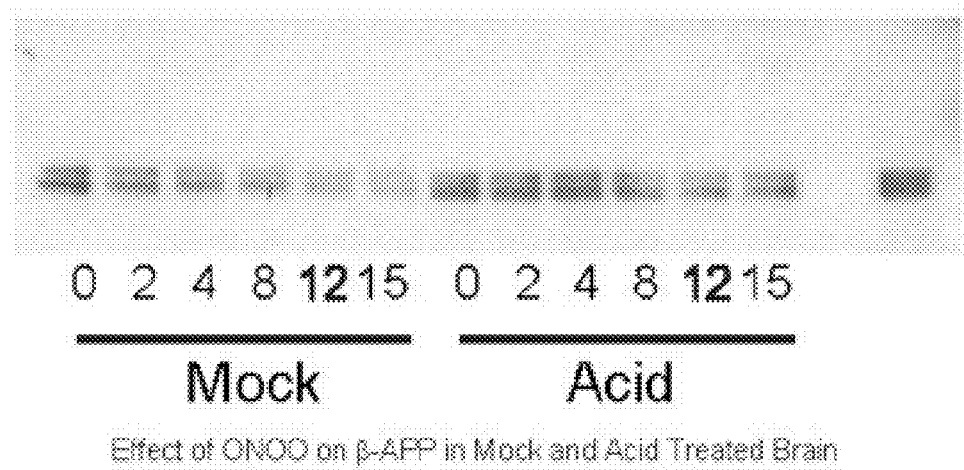
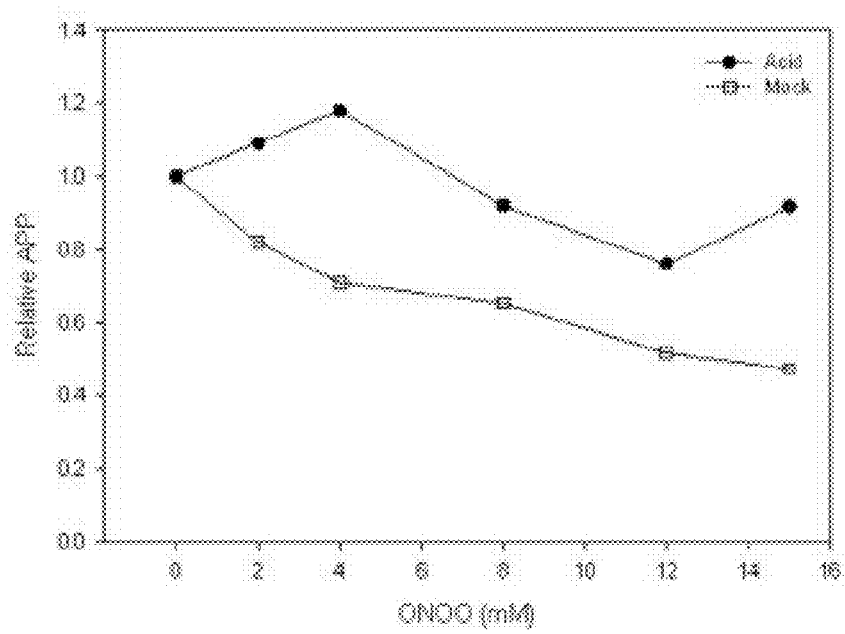

FIGURE 4 – CONTINUED
C
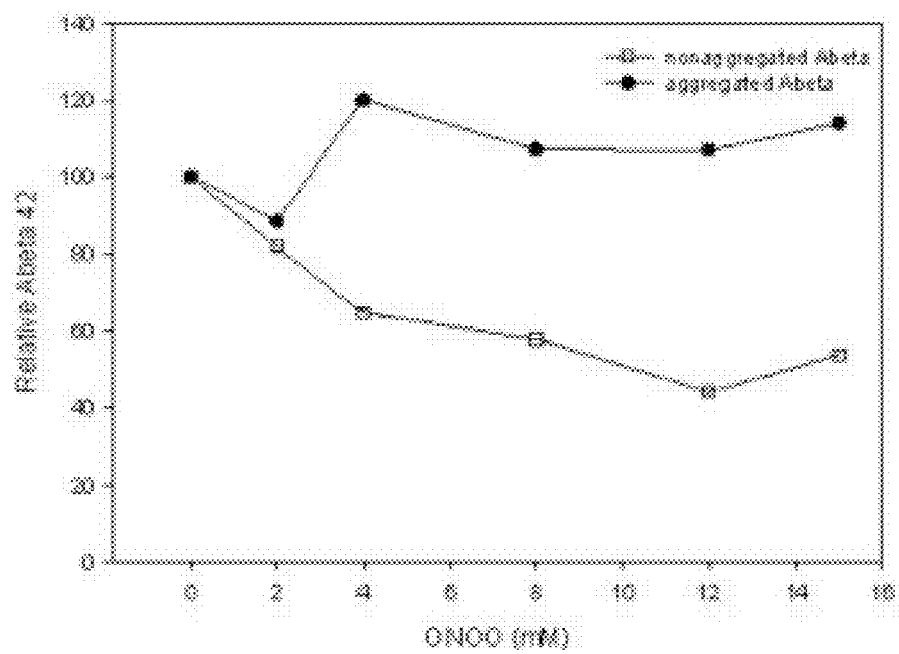

FIGURE 4- CONTINUED
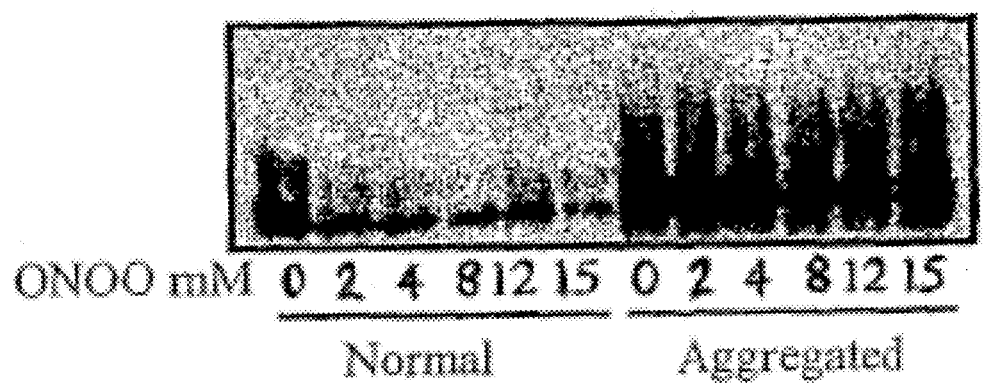
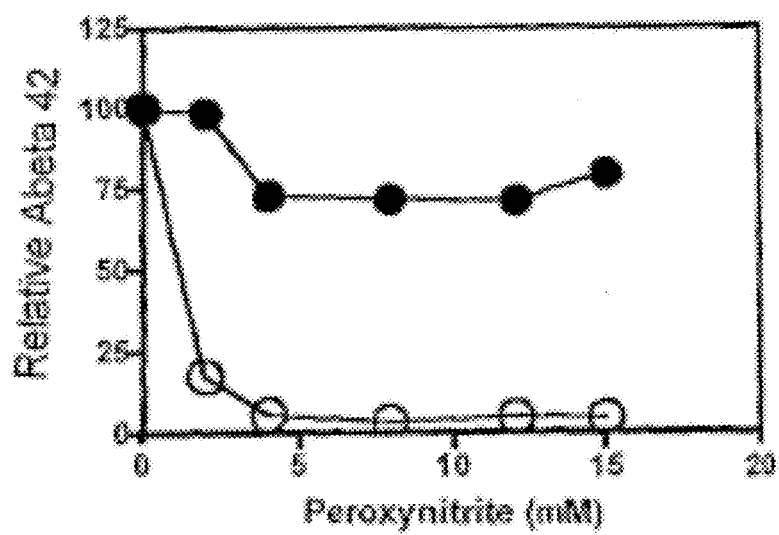

A 0   0.1µM   1µM   10µM   100µM   1mM   10mM

Native SOD1

B

A

| 0 | 0.1µM | 1µM | 10µM | 100µM | 1mM | 10mM | 0 | 0.1µM | 1µM | 10µM | 100µM | 1mM | 10mM |

Normal α-synuclein          Insoluble α-synuclein

B

ALS-SPECIFIC PEPTIDE COMPOSITION

CROSS REFERENCE TO RELATED APPLICATIONS

This application is a divisional of U.S. application Ser. No. 11/367,609, filed Mar. 3, 2006, which is a continuation-in-part of PCT/CA2004/001503, filed Aug. 20, 2004 (which designated the U.S.), which claims the benefit of U.S. provisional application Ser. No. 60/496,381 (now abandoned) and Canadian application serial no. 2,437,675, both filed Aug. 20, 2003, and U.S. provisional application Ser. No. 60/497,362 (now abandoned) and Canadian application serial no. 2,437,999, both filed Aug. 21, 2003, all of which are incorporated herein by reference in their entirety.

FIELD OF THE INVENTION

The invention relates to an epitope protection assay for use in diagnosis, prognosis and therapeutic intervention in diseases, for example, diseases involving polypeptide aggregation such as prion infections. The invention also relates to novel amyotrophic lateral sclerosis-specific epitopes, and their use to make novel antibodies. Further the invention includes the novel antibodies and uses thereof.

BACKGROUND OF THE INVENTION

Protein Misfolding and Aggregation

Proteins can fold into complex and close-packed structures. Folding is not only crucial for biological activity but failure of proteins to fold properly or remain folded can give rise to disease (Dobson C M, Methods (2004) 34:4-14). Misfolding can in some cases cause protein aggregation which can further give rise to discrete deposits extracellularly (e.g., plaques) or intracellularly (e.g., inclusions in the cytosol or nucleus).

Neurodegenerative diseases such as Alzheimer's disease (AD), Parkinson's disease (PD), Huntington's disease (HD), amyotrophic lateral sclerosis (ALS) and prion diseases are characterized by neural deposits of misfolded aggregated protein. Type II diabetes and some cancers have also been linked to protein misfolding and it is likely that there are yet to be identified diseases that result from errors in protein folding and that in some cases lead to consequences such as aggregation. The nature of the misfolding and any aggregation in such diseases is typically not well characterized.

Prion Diseases

Prion diseases have become a major health concern since the outbreak of BSE or "Mad Cow Disease" (reviewed above, 40, 41). BSE was first discovered in the United Kingdom but has now spread to many other countries in Europe and Japan. In the UK alone there has been close to 180,000 cases of BSE, which resulted in the destruction of cattle and possible infection of an estimated 3-5 million head. The total cost estimated to the UK was in excess of $2.5 billion. BSE is believed to be transmitted among cattle through feed that contains prions rendered from infected cattle, and it is thought to be transmitted to humans through eating beef or other cattle products from infected animals.

Emerging Prion Diseases

The prion diseases are a group of rapidly progressive and untreatable neurodegenerative syndromes, neuropathologically characterized by spongiform change, neuronal cell loss, gliosis, and brain accumulation of abnormal amyloid polypeptide. Human prion diseases include classical Creutzfeldt-Jakob disease (CJD), which has sporadic, iatrogenic, and familial forms. Since 1996, a "new variant" of CJD (vCJD) has been identified in the United Kingdom, France, the Republic of Ireland, Hong Kong, Italy, the United States, and Canada (40,41). Variant CJD is capable of killing individuals as young as age 14 with unknown incubation period. There is little doubt that vCJD is a human form of bovine spongiform encephalopathy (BSE)(42). The primary epidemic from consumption of contaminated cattle tissue has affected over 160 individuals as of this initial filing.

The spectre of vCJD "secondary epidemics" through blood, blood products, surgery, dentistry, vaccines, and cosmetics is of great concern (40,41). Detection of blood prion infectivity in experimental BSE/vCJD infections of mice and sheep (40) suggests a special risk exists for the transmission of vCJD through blood and blood products. The recent reports of vCJD prions recipients of donors who developed the disease is also troubling (52, 53). Canada and the United States have recently expanded vCJD blood donor deferrals to all countries in Western Europe.

Although sheep scrapie has been known for centuries, the most important animal prion disease at present is BSE. More than 173,000 cattle, primarily from Britain, have developed symptomatic BSE, and as many as 3 million have entered the food supply undetected. BSE is now being increasingly reported in cattle which were "born after the ban" in 1996 of food supplementation with meat and bone meal, suggesting that alternate routes may exist to keep the epidemic from being readily extinguished. Another troubling issue is the possible transmission of BSE to sheep, which may expose additional human populations to the BSE/vCJD prion strain. Recent reports show that prions can replicate in certain muscle groups of sheep, experimental animals and humans (54-57), indicating a potential risk in tissues previously considered safe for human consumption.

Chronic wasting disease (CWD) of captive and wild cervids (deer and elk) represents another newly emergent animal prion disease in North America, whose impact on human health is yet unknown. It is apparent that newly-recognized prion diseases pose a threat to the safety of foods, blood products, and medical-surgical treatments.

Prions: Atypical Pathogens

Newly emergent prion diseases, and the polypeptide-only nature of prions, have created serious medical, veterinary, and economic challenges worldwide. To date, the only commercialised tests for prion infection have been based on post-mortem brain samples. No biochemical test exists to detect prions in the blood of infected animals, despite detection by experimental transmission studies. The development of sensitive and specific diagnostic tests for prion infection is a challenging task, in part due to the unusual nature of the prion infectious agent. The infectious agents that transmit the prion diseases differ from other pathogens in that no nucleic acid component has been detected in infectious materials (41). According to the prion theory developed by Nobel Laureate Dr. Stanley Prusiner, infectivity resides in $PrP^{Sc}$, a misfolded conformational isoform of the near-ubiquitous normal cellular prion polypeptide $PrP^C$. $PrP^{Sc}$ is indeed the most prominent (or perhaps sole) macromolecule in preparations of prion infectivity, and minimally appears to be a reliable surrogate for prion infection. $PrP^{Sc}$ is partially resistant to protease digestion, poorly soluble, and exists in an aggregated state, in contrast to the protease sensitive, soluble, monomeric isoform $PrP^C$ (29, 31, 43-46).

$PrP^{Sc}$ is derived from its normal cellular isoform ($PrP^C$), which is rich in α-helical structure, by a posttranslational process involving a conformational transition. While the primary structure of $PrP^C$ is believed to be identical to that of $PrP^{Sc}$, secondary and tertiary structural changes are responsible for the distinct physicochemical properties of the two isoforms.

One of the difficulties in assessing the safety of food or blood products from potentially infected humans with prions is the lack of an accurate diagnostic test for blood or other accessible biosamples. Currently, there are no diagnostic tests that can be applied for screening live animals, humans, blood or blood products at an early stage. This also provides a further problem in organ transplantation, adding unknown risk to organ recipients. Therefore, as a preventative measure, countries such as the UK no longer source plasma from its inhabitants. The risk of spreading prion diseases has affected other countries as well. For example, the United States and Canada do not accept blood donations from individuals who have resided in the UK or France for more than 3-6 months.

Currently, the diagnosis of vCJD can only be confirmed following pathological examination of the brain at autopsy or biopsy. Some complimentary strategies in early CJD detection include electroencephalograms (EEG), magnetic resonance imaging (MRI) scans, and cerebrospinal fluid (CSF) tests, which may be useful "surrogate" or "proxy" markers. The absence of a "direct test" for prion infection stands in stark contrast to conventional infectious agents, such as viruses and bacteria.

Some tests that are in the process of being commercialized are based on surrogate markers of infection which are "once removed" from actual infectious prions.

PrP protease resistance is the basis of most commercially available diagnostic tests for prion disease. In the current methodologies, a sample of brain is removed and digested with proteases that can eliminate $PrP^C$, but leave a protease-resistant core of $PrP^{Sc}$. The protease-resistant fragment of $PrP^{Sc}$ is then detected by immunoblotting (as in the Prionics test) or by capture ELISA (as in the BioRad and Enfer tests, and in a new test from Prionics). However, digestion with proteases is cumbersome and variable, leading to false negatives and positives. Moreover, there are some prion strains which are reported to contain $PrP^{Sc}$ which is infectious and aggregated, but which is not protease resistant. Protease-sensitive $PrP^{Sc}$ also predominates early in infection and in cross-species transmission of disease (31).

Detection of protease-resistant PrP fragments is also the basis of a urine diagnostic test (47) which is being commercially developed by Prionics. However, detection of protease-resistant PrP in urine is subject to the same limitations as the post-mortem brain test, and has the additional disadvantage of requiring precipitation from large volumes of urine, and poor sensitivity (for example, only detecting $PrP^{Sc}$ in late stages of the disease, not pre-symptomatically).

Other Neurodegenerative Diseases

Neurodegenerative diseases, such as Alzheimer's disease (AD), Huntington's disease, amyotrophic lateral sclerosis (ALS) and Parkinson's disease/Lewy body dementia (PD, LBD) also pose major challenges to our aging population and health care system (reviewed in 1). An estimated 364,000 Canadians over 65 are currently diagnosed with AD or a related dementia (http://www.alzheimer.ca/). With increased life expectancy, the incidence of neurodegenerative disease is expected to grow. By 2025, AD will affect as many as a million Canadians, and by 2050, this number will double.

Sporadic AD, ALS, and PD/LBD are all associated with neural accumulation of pathological multimers of misfolded polypeptides (these could potentially be fibrils, protofilaments, and amorphous aggregates), including the amyloid-beta (Abeta) fragment of the amyloid precursor protein (APP) in AD; superoxide dismutase-1 (SOD1) in ALS, and alpha-synuclein in PD and LBD (1). Additionally familial amyloidotic polyneuropathy (FAP) results from the aggregation of transthyretin to form amyloid deposits. As with prion diseases, mutations in genes encoding these polypeptides are associated with autosomal dominant familial forms of AD, ALS, and PD.

Alzheimer's Disease

AD is a common dementing (disordered memory and cognition) neurodegenerative disease associated with brain accumulation of extracellular plaques composed predominantly of the Abeta (1-40), Abeta (1-42) and Abeta (1-43) peptides, all of which are proteolytic products of APP (reviewed in 4). In addition, neurofibrillary tangles, composed principally of abnormally phosphorylated tau protein (a neuronal microtubule-associated protein), accumulate intracellularly in dying neurons (4). Familial forms of AD can be caused by mutations in the APP gene, or in the presenilin 1 or 2 genes (www.websiteformutations.com), the protein products of which are implicated in the processing of APP to Abeta. Apolipoprotein E allelic variants also influence the age at onset of both sporadic and familial forms of AD (reviewed in 5). Abeta has been detected in the blood and CSF of AD patients and in normal controls (6). Abeta is also present in vascular and plaque amyloid filaments in trisomy 21 (Down's syndrome), hereditary cerebral hemorrhage with amyloidosis (HCHWA)-Dutch type, and normal brain aging (Mori, H et al. JBC (1992) 267: 17082-86). Tau and phosphorylated tau have been detected in the cerebral spinal fluid (CSF) of AD patients and patients with other neurological diseases (7; reviewed in 8).

Amyotrophic Lateral Sclerosis

Amyotrophic lateral sclerosis (ALS) is a fatal neuromuscular disease, with an incidence of 1 in 1000 adults, presenting as progressive weakness, muscle atrophy, and spasticity, which is due to degeneration of ~500,000 "lower motor neurons" in the spinal cord and brainstem, and innumerable "upper motor neurons" in the brain cortex. An important clue to the etiology of ALS came with the finding that about 20% of familial ALS (fALS) cases are due to mutations in superoxide dismutase-1 (SOD1) (10,11), a free radical defense enzyme. Over 100 fALS SOD1 missense, nonsense, and intronic splice-disrupting mutations have been catalogued to date (12; www.alsod.org). Transgenic mice expressing mutant human SOD1 (mtHuSOD1) develop a motor neuron syndrome with clinical and pathological similarities to human ALS (13, 14), whereas mice expressing wild-type human SOD1 (wtHuSOD1) do not develop disease (13). SOD1-containing cytoplasmic inclusions can be detected in many diseased motor neurons from familial and sporadic ALS patients (15), and in most transgenic mouse (16, 17) and tissue culture (18) models of the disease.

Parkinson's and Lewy Body Disease

PD is a neurodegenerative movement disorder second only to AD in prevalence (~350 per 100,000 population; 1). It is clinically characterized by rigidity, slowness of movement, and tremor (reviewed in 21). Most cases of Parkinson's disease are sporadic, but both sporadic and familial forms of the disease are characterized by intracellular Lewy bodies in dying neurons of the substantia nigra, a population of midbrain neurons (~60,000) that are selectively decimated in PD. Lewy bodies are predominantly composed of alpha-synuclein (22). Mutations in the gene encoding alpha-synuclein have been found in patients with familial Parkinson's disease (reviewed in 23; www.parkinsonsmutation.com). Another gene associated with autosomal recessive PD is parkin, which is involved in alpha-synuclein degradation (22, 23). Diffuse cortical Lewy bodies composed of alpha-synuclein are observed in Lewy body disease (LBD), a dementing syndrome associated with parkinsonian tone changes, hallucinations, and rapid symptom fluctuation (24). LBD may be the second most common form of neurodegenerative dementia after AD, accounting for 20 to 30 percent of cases among persons over the age of 60 years (1, 24).

Huntington's Disease and Related Diseases

HD is a progressive neurodegenerative disorder characterized by expansion of polyglutamine encoding CAG repeats in the N-terminus of the huntingtin protein (reviewed in 48). Polyglutamine stretches of $\geq 36$ cause disease and longer repeats cause earlier onset (49, 50).

Other polyglutamine diseases such as dentate-rubral and pallido-luysian atrophy (DRPLA) and some forms of sino-cerebellar ataxia (SCA) also have intracellular inclusions that roughly correlate to regions of neuronal death. Interruptions in the expanded polyglutamine repeat in the SCA-1 gene product result in the absence of disease (51), Neurodegenerative diseases, such as Alzheimer's disease (AD), amyotrophic lateral sclerosis (ALS) and Parkinson's disease/Lewy body disease (PD, LBD) pose major challenges to our aging population and health care system. No specific biochemical test exists for neurodegenerative diseases as a group (1,2). Since neurodegenerative diseases are regarded as "diagnoses of exclusion," very broad investigation is required to achieve "clinically probable" diagnosis for these progressive, incurable, and usually fatal conditions. Expensive surrogate testing, such as neuroimaging, is utilized to increase diagnostic probability (2). The availability of specific, sensitive, and inexpensive biochemical tests for this devastating group of diseases could potentially conserve financial resources for over-burdened health care systems. Moreover, secure diagnosis of these diseases at an earlier symptomatic stage increases the window for enhanced treatment efficacy at a time at which the disease pathophysiology is generally more responsive to treatment (3).

Effective, efficient and inexpensive diagnostic and screening strategies for antemortem diagnosis of human neurodegenerative diseases are urgently needed, given the aging population and continued financial pressure on the health care system.

Diabetes

Protein aggregation is also observed in patients with type II diabetes. Increased expression of the adipocyte-derived peptide, resistin, has been observed in diabetes type II patients (Youn B S et al. J Clin Endocrinol Metab. (2004); 89:150-6) and studies suggest that elevated resistin levels may play a role in obesity and insulin resistance. Additionally, islet amyloid polypeptide (also known as amylin) deposition is pathogenically associated with type 2 diabetes. These deposits contain islet amyloid polypeptide, a unique amyloidogenic peptide and are associated with beta cell death. Recent studies suggest that the species responsible for islet amyloid-induced beta-cell death are formed early in islet amyloid formation, when islet amyloid polypeptide accumulation begins (Hull R L et al. J Clin Endocrinol Metab. (2004) 89:3629-43). A diagnostic test that can identify pathogenic islet amyloid polypeptide would be very useful for detecting type 2 diabetes in its early stages, when dietary and therapeutic interventions are most effective.

Cancer

Many forms of cancer are also considered to be protein conformation diseases (Ishimaru D. et al. Biochemistry (2003) 42:9022-7). A subset of neuroblastomas, carcinomas and myelomas show an abnormal accumulation of tumor suppressor p53 protein aggregates (Butler J S et al. Biochemistry (2003) 42: 2396-403; Ishimaru D. et al. Biochemistry (2003) 42:9022-7). This accumulation could contribute to the loss of p53 function in some cancerous cells (Ishimaru D. et al. Biochemistry (2003) 42:9022-7). Assays able to detect accumulated p53 could provide a diagnostically useful detection system and could enhance therapeutic intervention by individualizing therapeutic intervention.

SUMMARY OF THE INVENTION

The inventor has recently developed the epitope protection assay (EPA), a novel method that yields sensitive and specific antemortem detection of disease proteins in blood and other accessible tissues and fluids. The invention shows the role of aggregation in diseases, such as prion disease and amyotrophic lateral sclerosis, and provides an assay that overcomes problems in the prior art. In prion diseases, the normal cellular monomeric prion polypeptide $PrP^C$ undergoes refolding to an abnormal, aggregated isoform, generically designated $PrP^{Sc}$. Diseases such as AD, PD, LBD, ALS and HD are also characterized by misfolded and/or aggregated conformations of cellular proteins. This property is exploited by the methods of the invention to provide sensitive and specific diagnostic tests for these and other diseases.

According to the invention, the methods are useful where a target epitope is accessible in either one of a non-wildtype protein (i.e. disease protein) or a wild type protein and inaccessible in the other. Inaccessibility is often due to aggregation making the target epitope inaccessible.

In one embodiment, the non-wildtype protein confirmation is indicative of a disease associated with protein aggregation, such as amyotrophic lateral sclerosis.

The invention includes a method of detecting whether a candidate polypeptide including a target epitope is a disease (disorder) polypeptide or a wild type polypeptide, comprising:

contacting the candidate polypeptide with a blocking agent; and determining whether the target epitope is inaccessible or accessible to chemical modification by the blocking agent.

The accessibility or inaccessibility of the target epitope is indicative of whether the candidate polypeptide is a disease (disorder) polypeptide or a wild type polypeptide because in one of the disease (disorder) protein and the wild type protein, the target epitope is accessible. In the other polypeptide the target epitope is inaccessible.

In one embodiment, the invention provides a method of detecting prion diseases, for example, determining whether a candidate polypeptide including a target epitope is in a wild-type conformation or in a non-wildtype conformation in which it is aggregated, comprising:

reacting a sample of polypeptide (the sample typically contains $PrP^{Sc}$ and/or $PrP^C$, and in many cases an abundance of one or the other) with a chemical modifying agent, typically an agent which chemically reacts with proteins such as peroxynitrite, which modifies accessible epitopes (target epitopes) so that they cannot bind to a detection agent;

disaggregating and/or denaturing the polypeptide in the sample; and probing with detection agents, such as an antibody against a target epitope, to determine whether the polypeptide (such as prior to disaggregation and/or denaturing) included inaccessible target epitopes.

$PrP^C$ is rendered "invisible" in the assay, because epitopes on the monomeric molecules are blocked to antibody recognition by the chemical modifying agent, whereas molecules of $PrP^{Sc}$ are "protected" from chemical modification by virtue of being sequestered within aggregates or otherwise unavailable for reacting. Alternatively, epitopes on the multimeric molecules are blocked to antibody recognition by the chemical modifying agent, whereas molecules of $PrP^C$ are "protected" from chemical modification by virtue of a difference in accessible epitopes.

In another embodiment, the Alzheimer's disease detection method comprises:

reacting a sample of polypeptide (the sample typically contains all or part of diseased amyloid precursor polypeptide or A beta or tau and/or the corresponding wild type polypeptide, and in many cases an abundance of one or the other) with a chemical modifying agent, typically an agent which chemically reacts with proteins such as peroxynitrite, which modifies exposed epitopes so that they cannot bind to a detection agent;

disaggregating and/or denaturing the polypeptide in the sample; and probing with detection agents, such as an antibody against a target epitope to determine whether the polypeptide prior to disaggregation and/or denaturing, included inaccessible target epitopes.

In further embodiments, the invention provides disease detection methods for other diseases characterized by differentially accessible target epitopes in disease and wildtype conformations, for example, resulting from misfolded and/or aggregated proteins such as Parkinson's disease (PD), Lewy Body disease (LBD), Huntington's disease (HD), amyotrophic lateral sclerosis (ALS), diabetes, and cancer. These methods similarly include steps such as reacting a sample of polypeptide (eg. a disease polypeptide described herein) with a chemical modifying agent, which modifies exposed epitopes so that they cannot bind to a detection agent; then disaggregating and/or denaturing the polypeptide in the sample; and probing with detection agents, such as an antibody against a target epitope to determine whether the polypeptide prior to disaggregation and/or denaturing, included inaccessible target epitopes. These steps are similarly adapted for other purposes, such as screening blood and blood products, and other uses described herein.

The method of the invention has many advantages over existing technology. As noted above, the invention is optionally referred to as "EPA", which in the case of prion protein disease detection is a simple, efficient method for detecting aggregated disease proteins such as $PrP^{Sc}$, the pathogenic molecule which is thought to constitute the infectious particle in prion diseases and Abeta peptide, associated with AD.

The invention is useful in high-throughput robotic-capable platforms. For example, EPA is not dependent on PrP protease resistance, the basis of most commercially available diagnostic tests for prion disease. Epitope protection technology does not require a protease digestion step, which makes it more sensitive to early infection. Certainly, the absence of a protease digestion step permits EPA to be more amenable to high-throughput robotic platforms.

In addition, the methods of the invention can be used to detect any protein that exists in two or more conformations, where one or more target epitopes are concealed in at least one conformation.

Accordingly, the invention relates to a detection method comprising:

reacting a sample of polypeptide with a chemical modifying agent, typically an agent which chemically reacts with proteins, which is defined to modify exposed epitopes so that they cannot bind to detection agents;

disaggregating and/or denaturing the polypeptide in the sample; and probing with detection agents, such as antibodies against a target epitope to determine whether the polypeptide prior to disaggregation and/or denaturing, included target epitopes inaccessible to the chemical modifying agent.

The result indicates whether the polypeptide includes inaccessible epitopes, which is indicative of the type of polypeptide that is present (i.e. wild type protein or non-wild type protein).

In one embodiment, the invention includes a method of detecting whether a candidate polypeptide including a target epitope is in a wildtype conformation or a non-wildtype conformation (in one embodiment, in the non-wildtype conformation, the candidate polypeptide aggregates with aggregated polypeptide), comprising:

contacting the polypeptide with a blocking agent that selectively blocks accessible target epitopes, wherein in one of the non-wildtype conformation or the wildtype conformation, the target epitope is accessible and reacts with the blocking agent, and wherein in the other conformation, the target epitope is inaccessible and does not react with the blocking agent. Unreacted blocking agent is removed from contact with the polypeptide, for example, by allowing time for blocking agent to be consumed or degraded or by actively removing it by physical or chemical processes as described below;

modifying the candidate polypeptide to convert any inaccessible target epitope to accessible target epitope; and contacting the polypeptide with a detection agent that binds selectively to target epitope that was converted from inaccessible target epitope to accessible target epitope, wherein binding between detection agent and converted target epitope indicates that prior to conversion the candidate polypeptide was in a conformation in which the target epitope was inaccessible and wherein lack of binding between the detection agent and the target epitope indicates that the polypeptide was in a conformation in which the target epitope was accessible, thereby indicating whether the polypeptide was in a wildtype conformation or a non-wildtype conformation.

The invention also includes a method of detecting whether a candidate polypeptide including a target epitope is in a wildtype conformation or a non-wildtype conformation, comprising:

contacting the polypeptide with a blocking agent that selectively blocks accessible target epitope, wherein in the wildtype conformation, the target epitope is accessible and reacts with the blocking agent, and wherein in the non-wildtype conformation, the target epitope is inaccessible and does not react with the blocking agent. Unreacted blocking agent is removed from contact with the polypeptide, for example, by allowing time for blocking agent to be consumed or degraded or by actively removing it by physical or chemical processes as described below;

modifying the candidate polypeptide to convert any inaccessible target epitope to accessible target epitope; and contacting the polypeptide with a detection agent that binds selectively to the target epitope that was converted from inaccessible target epitope to accessible target epitope, wherein binding between detection agent and converted target epitope indicates that the candidate polypeptide was in a non-wildtype conformation and wherein lack of binding between the detection agent and the target epitope indicates that the polypeptide was in a wildtype conformation.

The invention also includes a method of detecting whether a candidate polypeptide including a target epitope is in a wildtype conformation or a non-wildtype conformation, comprising:

contacting the polypeptide with a blocking agent that selectively blocks accessible target epitope, wherein in the non-wildtype conformation, the target epitope is accessible and reacts with the blocking agent, and wherein in the wildtype conformation, the target epitope is inaccessible and does not react with the blocking agent. Unreacted blocking agent is removed from contact with the polypeptide, for example, by allowing time for blocking agent to be consumed or degraded or by actively removing it by physical or chemical processes as described below;

modifying the candidate polypeptide to convert any inaccessible target epitope to accessible target epitope; and contacting the polypeptide with a detection agent that binds selectively to target epitope that was converted from inaccessible target epitope to accessible target epitope, wherein binding between detection agent and converted target epitope indicates that the candidate polypeptide was in a wildtype conformation and wherein lack of binding between the detection agent and the target epitope indicates that the polypeptide was in a non-wildtype conformation.

The invention also includes a method of detecting whether a candidate polypeptide including target epitope which has been reacted with a blocking agent, is in a wildtype conformation or a non-wildtype conformation, comprising:

modifying the candidate polypeptide to convert any inaccessible target epitope to accessible target epitope;

contacting the polypeptide with a detection agent that binds selectively to the target epitope that was converted from inaccessible target epitope to accessible target epitope, wherein binding between detection agent and converted target epitope indicates that the candidate polypeptide was in a non-wildtype conformation and wherein lack of binding between the detection agent and the target epitope indicates that the polypeptide was in a wild type conformation.

In the methods of the invention, the epitope is in many cases inaccessible in the misfolded or non-wild type conformation because i) the differential misfolding of the polypeptide compared to the wild type folded polypeptide prevents or reduces reaction between the blocking agent and the target epitope, ii) the polypeptide in the misfolded conformation aggregates with itself or other polypeptides in the misfolded conformation to prevent or reduce reaction between the protecting/blocking agent and the target epitope, and/or iii) post translational modifications of the polypeptide prevent or reduce reactions between the blocking agent and the target epitope.

In one example, the candidate polypeptide comprises prion protein, the wild type folded conformation comprises the conformation of wild type folded prion protein and the misfolded conformation comprises the conformation of PrP$^{Sc}$. Alternatively, the wild type folded protein comprises the conformation of APP or its cleavage product amyloid beta, and the misfolded conformation comprises the conformation of Alzheimer's disease APP or its cleavage product amyloid beta.

In another example, the candidate polypeptide comprises, SOD1, alpha-synuclein, islet amyloid polypeptide, resistin or p53 protein. The methods and kits of the invention described in the application are useful, for example, for application to a non-wildtype polypeptide having a conformation comprising multiple copies of a polypeptide aggregated together through interactions of beta-sheet-rich areas of the polypeptide. In one embodiment the polypeptide is polypeptide that is aggregated in prion protein aggregates. In another embodiment, the polypeptide is polypeptide that is aggregated in amyloid plaques.

The invention also includes i) polypeptide of the invention modified by reaction with a blocking agent listed herein and ii) the polypeptide modified by reaction with a detecting agent. The invention also includes compositions and kits of the invention including these modified polypeptide.

The blocking agent is optionally peroxynitrite, hydrogen peroxide, diethyl pyrocarbonate (DEPC), 4-hydroxynonenal (4HNE) an epoxide such as conduritol-B-epoxide and 1,2-epoxy-3-(p-nitrophenoxy)propane, methylene or diazirine and related compounds. In the methods, the polypeptide is optionally modified by denaturing the polypeptide, for example with heat, detergent and/or chaotropic agents. The polypeptide is optionally modified by treatment with a disaggregation agent to disaggregate the polypeptide from other polypeptides of the same type, and from other molecules, wherein the disaggregation agent is optionally selected from at least one of the group consisting of chaotropic agent (including guanidine salts, urea or thiourea), detergent and heat.

It is readily apparent to a skilled person that the method steps of the invention recited here involving removing the blocking agent typically involve physically, chemically or otherwise removing the blocking agent away from the candidate polypeptide to prevent further reaction. Removal optionally involves allowing a sufficient time to pass so that the blocking agent is removed from the candidate polypeptide by being consumed or degraded (for example, such that the blocking agent becomes inert or oxidized). Removal optionally involves adding a compound to react with any excess blocking agent to inactivate it. Removal also optionally involves physical filtering of the blocking agent by conventional filtration techniques or centrifugation to separate the candidate polypeptide and blocking agent, or physical binding to a substrate useful for removing the blocking agent, such as by binding of blocking agent or candidate polypeptide to an immobilized substrate in a column.

Removing means preventing further reactions by the blocking agent by, for example, physically or chemically inactivating the blocking agent, taking the blocking agent out of contact with the sample including the candidate polypeptide or allowing a sufficient amount of time to pass for the blocking agent to be consumed or degraded.

The detection agent optionally comprises an antibody directed against a prion polypeptide epitope, an amyloid beta epitope, an alpha-synuclein epitope or a SOD1 epitope. The antibody optionally comprises all or part of the anti-prion antibodies 6H4 and 3F4, and the anti-amyloid beta antibodies 6E10 and 4G8.

The methods of the invention are preferably used with mammals, such as humans. In addition, the methods of the invention are preferably used with mammals, such as livestock. In addition the methods of the invention are used with food items, cosmetic items, dental and surgical instruments vacuums and pharmaceutical products.

The invention also includes a method of testing a sample from an animal, using methods of the invention described herein, to determine if the animal has a disease characterized by the presence of candidate polypeptide in a non-wildtype conformation in the sample, wherein the candidate polypeptide includes a target epitope. Such diseases are described herein. In one embodiment, the method comprises; determining whether the candidate polypeptide is in i) a wildtype conformation or ii) a non-wildtype conformation, by a method comprising the steps of:

contacting the sample with a blocking agent that selectively blocks accessible target epitope in the candidate polypeptide, wherein in the wildtype conformation, the target epitope is accessible and reacts with the blocking agent, and wherein in the non-wildtype conformation, the target epitope is inaccessible because the candidate polypeptide is aggregated with the aggregated polypeptide and the target epitope cannot react with the blocking agent;

contacting the sample with a conversion agent to modify the candidate polypeptide to convert any inaccessible target epitope in the sample to accessible target epitope;

contacting the polypeptide with a detection agent that binds selectively to target epitope that was converted from inaccessible target epitope to accessible target epitope, wherein binding between detection agent and converted target epitope indicates that the candidate polypeptide was in a non-wildtype conformation and the animal has a disease and wherein lack of binding between the detection agent and the target epitope indicates that the polypeptide was in a wild type conformation.

The invention also includes a method of the invention described herein for screening, for example, by testing a sample, such as blood or blood products and other samples, to determine if the sample comprises a candidate polypeptide in a non-wildtype conformation wherein the candidate polypeptide includes a target epitope. In one embodiment, the method comprises; determining whether the candidate polypeptide is in i) a wildtype conformation or ii) a non-wildtype conformation, by a method comprising the steps of:

contacting the sample with a blocking agent that selectively blocks accessible target epitope in the candidate polypeptide, wherein in the wildtype conformation, the target epitope is accessible and reacts with the blocking agent, and wherein in the non-wildtype conformation, the target epitope is inaccessible and cannot react with the blocking agent;

contacting the sample with a conversion agent to modify the candidate polypeptide to convert any inaccessible target epitope in the sample to accessible target epitope;

contacting the polypeptide with a detection agent that binds selectively to target epitope that was converted from inaccessible target epitope to accessible target epitope, wherein binding between detection agent and converted target epitope indicates that the candidate polypeptide was in a non-wildtype conformation and the sample comprises a candidate polypeptide in a non-wildtype conformation and wherein lack of binding between the detection agent and the target epitope indicates that the polypeptide was in a wild type conformation.

In another embodiment, the invention relates to a method of detecting whether a candidate polypeptide including a target epitope is in i) a wildtype conformation or ii) a non-wildtype conformation (for example, wherein the polypeptide aggregates in the non-wildtype conformation), comprising:

contacting the polypeptide with a blocking agent that selectively blocks accessible target epitope, wherein in the wildtype conformation, the target epitope is accessible and reacts with the blocking agent, and wherein in the non-wildtype conformation, the target epitope is inaccessible (for example, because the candidate polypeptide is aggregated) and the target epitope cannot react with the blocking agent;

modifying the candidate polypeptide to convert inaccessible target epitope to accessible target epitope; and contacting the polypeptide with a detection agent that binds selectively to the target epitope that was converted from inaccessible target epitope to accessible target epitope, wherein binding between detection agent and converted target epitope indicates that the candidate polypeptide was in a non-wildtype conformation and wherein lack of binding between the detection agent and the target epitope indicates that the polypeptide was in a wild type conformation. One also removes unreacted blocking agent from contact with the polypeptide, for example, by allowing it to be consumed or degraded or removing it from the reaction by physical or chemical processes.

The candidate polypeptide optionally comprises prion protein, the wild type conformation comprises the conformation of wild type prion protein and the non-wildtype conformation comprises the conformation of $PrP^{Sc}$. The candidate polypeptide optionally comprises beta-amyloid polypeptide, tau protein or APP protein, SOD1, alpha-synuclein, huntingtin protein, p53 or islet amyloid polypeptide or resistin. The blocking agent is optionally selected from the group consisting of peroxynitrite, hydrogen peroxide, methylene compounds, succinic anhydride, epoxides, diethyl pyrocarbonate, 4-hydroxynonenal (4HNE) and diazirine. The polypeptide is optionally modified by denaturing the polypeptide. The polypeptide is also optionally denatured by heat and/or detergent and/or chaotropic agents. The polypeptide is optionally modified by treatment with a disaggregation agent to disaggregate the polypeptide from the aggregated polypeptides. The disaggregation agent is optionally selected from at least one of the group consisting of chaotropic agents, detergent and heat. The detergent optionally comprises SDS. The detection agent optionally comprises an aptamer or an antibody, for example, directed against a prion polypeptide epitope. The antibody optionally comprises 6H4 or 3F4. The aptamer or antibody is optionally directed against an amyloid beta epitope. The antibody optionally comprises 6E10 or 4G8. The non-wildtype conformation is in certain embodiments indicative of a disease caused by protein aggregation, such as prion disease (eg. BSE or CJD), Alzheimer's disease, Parkinson's disease or Lewy body disease, Huntington's disease, amyotrophic lateral sclerosis, cancer or diabetes. Optionally, prior to contacting the blocking agent with the candidate polypeptide, the candidate polypeptide is in a sample that is pretreated by one or more of the following methods: adsorption, precipitation, or centrifugation. Optionally, prior to contacting the blocking agent with the candidate polypeptide, the target epitope is mapped (i.e., the epitope is identified, for example, as described below under the "Target Epitopes" section). Optionally, the polypeptide is in a postmortem or antemortem sample selected from the group of: CSF, serum, blood, urine, biopsy sample or brain tissue. Another aspect of the invention relates to a kit for detecting whether a candidate polypeptide including a target epitope is in i) a wildtype conformation or ii) a non-wildtype conformation, comprising a detecting agent that recognizes the target epitope and instructions for at least one of i) mapping a target epitope, ii) contacting a candidate polypeptide with a blocking agent, and iii) contacting a candidate polypeptide with a detecting agent. The kit is useful to implement method of the invention described herein. The detecting agent optionally comprises an aptamer or an antibody. The antibody optionally comprises 6H4, 3F4, 6E10 or 4G8, optionally immobilized to a solid support. The kit optionally further comprises buffers and reagents, for example, for ELISA, such as sandwich ELISA, fluorescent ELISA. The kit optionally further comprises a blocking agent. The kit optionally further comprises a denaturing agent selected from at least one of the group of detergents and chaotropic agents. The kit optionally further comprises a polypeptide standard. The kit optionally comprises a recombinant disease protein or a recombinant protein that mimics a disease protein. In another embodiment, the invention relates to method of detecting whether a candidate polypeptide that has been contacted with a blocking agent is i) a wildtype conformation or ii) a non-wildtype conformation, wherein the candidate polypeptide comprises at least one target epitope and, following contact with the blocking agent and removal of the blocking agent, the candidate polypeptide has been modified to convert any inaccessible target epitope to accessible target epitope, the method comprising: contacting the polypeptide with a detection agent that binds selectively to the target epitope that was converted from inaccessible target epitope to accessible target epitope, wherein binding between detection agent and converted target epitope indicates that the candidate polypeptide was in a non-wildtype conformation (for example, an aggregated conformation) and wherein lack of binding between the detection agent and the target epitope indicates that the polypeptide was in a wild type conformation. Diseases, blocking agents, target epitopes, detecting agents and other aspects described herein are also useful in this method. The diseases, blocking agents, target epitopes, detecting agents and other aspects described herein are also readily adapted for the methods described in preceding paragraphs, such as methods for testing a sample from an animal (such as a human, livestock etc.) to determine if the animal has a disease or screening a sample.

The reverse situation to the methods described in some of the aforementioned paragraphs is also usefully detected, for example, where the wildtype conformation includes an inaccessible epitope and the non-wild type conformation has an accessible epitope. This situation is also readily adapted to methods described herein, such as diagnosing disease or screening samples.

The inventor has also identified and targeted ALS-specific epitopes that are present or antibody-accessible on ALS-associated forms of SOD1, but not on the native homodimeric form of SOD1. Such ALS-specific epitopes are those presented uniquely by the dissociated, monomeric form of SOD1, and all misfolded forms of SOD1 in monomeric, dimeric or aggregated form, but not on the molecular surface of native dimeric forms of SOD1. These novel epitopes can be used to elicit an immune response in an animal, for example to make antibodies specific for the epitope. Thus, the epitopes can also be defined as those epitopes that give rise to antibodies that bind selectively to the to the ALS-associated forms of SOD1, relative to the native homodimeric form of SOD1.

Thus, the invention includes compositions for eliciting an immune response in an animal comprising an effective amount of an isolated ALS-specific epitope in admixture with a suitable diluent or carrier,
wherein the ALS-specific epitope comprises an isolated peptide selected from the group consisting of:

```
DLGKGGNEESTKTGNAGS;       (SEQ ID NO: 1)
and

NPLSRKHGGPKDEE.           (SEQ ID NO: 2)
```

Another aspect of the invention is a composition for eliciting an immune response in an animal comprising an effective amount of a nucleic acid encoding an isolated ALS-specific epitope in admixture with a suitable diluent or carrier,
wherein the ALS-specific epitope comprises an isolated peptide selected from the group consisting of:

```
DLGKGGNEESTKTGNAGS;       (SEQ ID NO: 1)
and

NPLSRKHGGPKDEE.           (SEQ ID NO: 2)
```

The invention also includes isolated antibodies made using the compositions of the invention and antibodies specific for an ALS-specific epitope, wherein the ALS-specific epitope comprises an isolated peptide selected from the group consisting of:

```
DLGKGGNEESTKTGNAGS;       (SEQ ID NO: 1)
and

NPLSRKHGGPKDEE.           (SEQ ID NO: 2)
```

A further aspect of the invention is a method for eliciting an immune response in an animal using the compositions of the invention, and methods for making antibodies using the compositions of the invention.

The antibodies of the invention can be used in EPA. Thus, one aspect of the invention is a method of detecting whether a candidate polypeptide including a target epitope is in i) a wildtype conformation or ii) a non-wildtype conformation, wherein the candidate polypeptide is SOD1, and wherein the non-wildtype conformation is an aggregated form of SOD1, comprising:
contacting the polypeptide with a blocking agent that selectively blocks accessible target epitope, wherein in the wildtype conformation, the target epitope is accessible and reacts with the blocking agent, and wherein in the non-wildtype conformation, the target epitope is inaccessible and the target epitope cannot react with the blocking agent;
removing unreacted blocking agent from contact with the polypeptide;
modifying the candidate polypeptide to convert any inaccessible target epitope to accessible target epitope; and
contacting the polypeptide with a detection agent that binds selectively to the target epitope that was converted from inaccessible target epitope to accessible target epitope,
wherein binding between detection agent and converted target epitope indicates that the candidate polypeptide was in a non-wildtype conformation and wherein lack of binding between the detection agent and the target epitope indicates that the polypeptide was in a wild type conformation, and wherein the detection agent comprises an antibody specific for an ALS-specific epitope.

Another aspect of the invention is a method of detecting whether a candidate polypeptide including a target epitope is in i) a wildtype conformation or ii) a non-wildtype conformation, comprising:

contacting the polypeptide with a blocking agent that selectively blocks accessible target epitope, wherein in the non-wildtype conformation, the target epitope is accessible and reacts with the blocking agent, and wherein in the wildtype conformation, the target epitope is inaccessible and the target epitope cannot react with the blocking agent;

removing unreacted blocking agent from contact with the polypeptide;

modifying the candidate polypeptide to convert any inaccessible target epitope to accessible target epitope; and contacting the polypeptide with a detection agent that binds selectively to the target epitope that was converted from inaccessible target epitope to accessible target epitope, wherein binding between detection agent and converted target epitope indicates that the candidate polypeptide was in a wildtype conformation and wherein lack of binding between the detection agent and the target epitope indicates that the polypeptide was in a non-wildtype conformation, and wherein the detection agent comprises an antibody specific for a target epitope on SOD1 that is inaccessible to blocking agent.

The antibodies specific for the ALS-specific epitope can also be used to detect ALS-associated forms of SOD1. These ALS-associated forms of SOD1 present an antibody-accessible epitope that is not present on the molecular surface of native dimeric SOD1. The ALS-specific epitopes thus can be presented by monomeric SOD1, and by misfolded SOD1 in monomeric, dimeric or aggregate form, and thereby can be used to diagnose amyotrophic lateral sclerosis. In one embodiment of the invention, the method includes detecting or diagnosing amyotrophic lateral sclerosis in a subject comprising the steps of:

(a) contacting a test sample of said subject with any one of the antibodies of the invention, wherein the antibody binds to an ALS-specific epitope to produce an antibody-antigen complex;

(b) measuring the amount of the antibody-antigen complex in the test sample; and (c) comparing the amount of antibody-antigen complex in the test sample to a control wherein a difference in the amount of antibody-antigen complex in the test sample as compared to the control is indicative of amyotrophic lateral sclerosis.

These antibodies can also be conjugated to labels to produce a diagnostic agent.

The invention also includes kits comprising the compositions and antibodies of the invention to elicit an immune response in an animal; or to detect monomeric or misfolded SOD1, and thereby to diagnose amyotrophic lateral sclerosis.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

Embodiments of the invention are described in relation to the drawings in which.

The 6E10 epitope in the Abeta region of APP is less accessible to peroxynitrite modification in Alzheimer's disease brain compared to normal brain (panel A), and in brain homogenates that have been treated at low pH to induce protein aggregation (panel B). Abeta 1-42 peptide aggregated in vitro shows prominent epitope protection of the 6E10 epitope to peroxynitrite modification, in comparison with soluble non-aggregated Abeta 1-42 (panel C). Normal and aggregated Abeta 1-42 treated with increasing concentrations of peroxynitrite and them immunoblotted with 6E10 antibody also shows prominent epitope protection (panel D).

Figure 5:
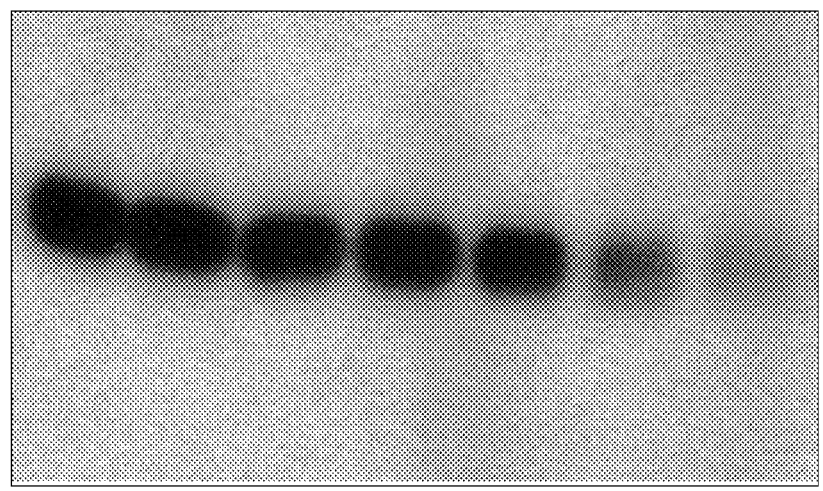
Figure 5:
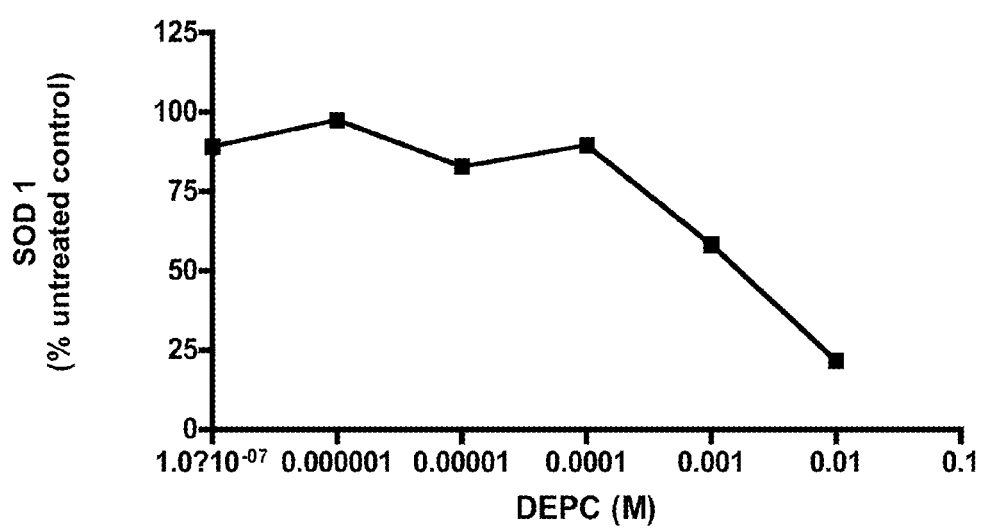

FIG. 5 Detection of epitopes modifiable by DEPC in SOD1

(A) Western blot showing soluble SOD1 treated with increasing concentrations of DEPC and immunoblotted with sheep anti-SOD1. (B) Graphical representation of decreasing antibody binding to SOD1 with increasing DEPC-concentration.

Figure 6:
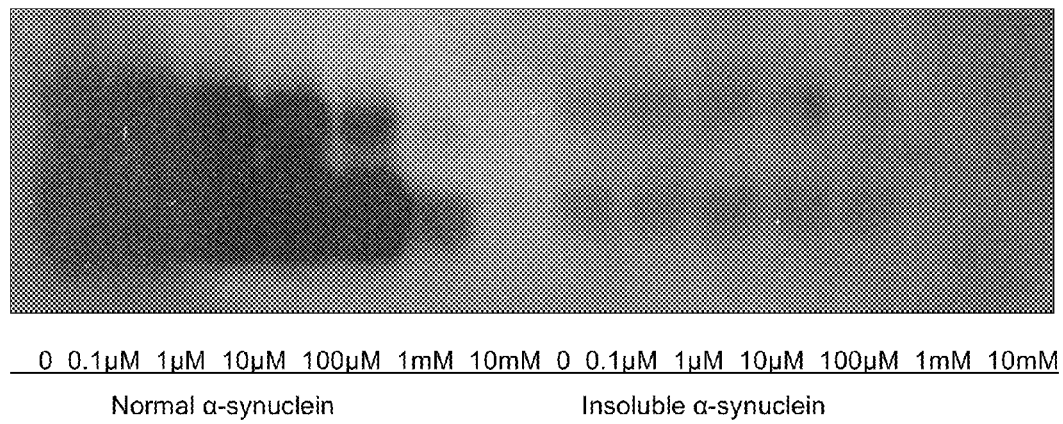
Figure 6:
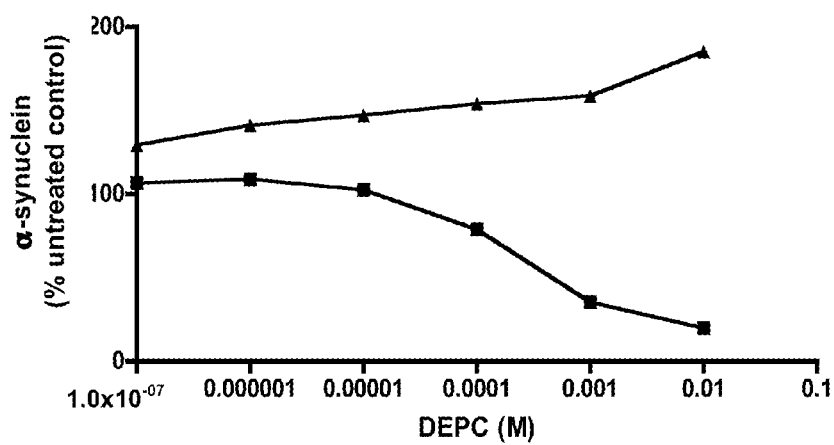

FIG. 6 Detection of aggregated alpha-synuclein using EPA (A) Western blot showing effect of increasing concentrations of DEPC on antibody binding to soluble and insoluble alpha-synuclein. (B) Graphical representation showing the extent of antibody binding to normal (■) and insoluble (▲) alpha-synuclein.

DETAILED DESCRIPTION OF THE INVENTION

The current invention provides a useful method for the detection of a disease related polypeptide counterpart of a normal cellular polypeptide which forms aggregates or otherwise leads to the obscuration of one or more epitopes that are not obscured in the normal or wild type polypeptide. The invention recognizes the importance of aggregation in the pathology of diseases such as prion disease and amyotrophic lateral sclerosis. The invention also takes advantage of this aggregation effect and provides an assay that overcomes problems with prior art detection assays. In one embodiment, the method of the invention is applied to the detection of $PrP^{Sc}$ in plasma, serum, urine or other biological sample. The methods of the invention are further useful for detecting any polypeptide that exists in two or more conformations, where one or more target epitopes are inaccessible in at least one conformation. In one embodiment the invention includes a method of detecting whether a candidate polypeptide including a target epitope is in a wild type or non-wild type conformation.

"Epitope" refers to a portion of a sequence of contiguous or non-contiguous amino acids (antigen) which is recognized by and bound by a detection agent such as an antibody. Preferably, the epitope is a linear epitope on a polypeptide which typically includes 3 to 10 or 6 to 10 or more contiguous amino acids that are recognized and bound by a detection agent. A conformational epitope includes non-contiguous amino acids. Sometimes conformational epitopes can re-establish themselves after denaturation by partial refolding on, e.g., an immunoblot membrane. The detection agent such as an antibody recognizes the 3-dimensional structure. When a protein molecule is folded into a three dimensional structure the amino acids forming the epitope are positioned in a manner that permits the detection agent to recognize and bind to the amino acids. In an unfolded (denatured) protein only the linear epitope is recognized and bound by the detection agent. Since the protein is unfolded prior to contact with the detection agent, the inaccessible epitope will typically be a linear epitope.

"Blocking agent" refers to an agent that reduces epitope reactivity, for example by binding to the epitope or by modifying and destroying epitope reactivity, for example on an amino acid side group within a linear epitope, so that the epitope is prevented from binding to detection agent (usually but not always an antibody). An example of a blocking agent is peroxynitrite. Other examples would include methylene, hydrogen peroxide, diethyl pyrocarbonate, 4-hydroxynonenal (4HNE) epoxides such as conduritol-B-epoxide and 1,2-epoxy-3-(p-nitrophenoxy)propane and diazirine. Chemical modifying agents that saturate accessible amino acids critical for epitope recognition in native conditions are most useful in the applications of epitope protection technology. Additionally the blocking agent may phosphorylate, glycosylate or otherwise modify a target-epitope. The blocking agent may also include peptides, antibodies or antibody fragments that bind to the epitope. The blocking agent should efficiently modify accessible amino acids (e.g. modify at least: 50%, 75%, 90%, 95% or 99% of accessible amino acids).

"Accessible epitope" is target epitope that is available to react with blocking agent in methods of the invention. For example, epitope that is available to react with blocking agent is accessible epitope. After reacting with blocking agent, the accessible epitope is prevented from binding to detection agent (after this reacting step, the reacted epitope may be referred to as the blocked epitope).

"Antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')$_2$, scFv, dsFv, ds-scFv, dimers, minibodies, diabodies, and multimers thereof and bispecific antibody fragments. Antibodies can be fragmented using conventional techniques and the fragments screened for utility in the same manner as described below. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques.

"Antibody-accessible" as used herein refers to an epitope on a polypeptide that is available to specifically bind with an antibody. In a preferred embodiment, the novel ALS-specific epitopes are antibody-accessible on ALS-associated forms of SOD1, but not on the native homodimeric form of SOD1.

"Aptamer" means a macromolecule such as a peptide, RNA or DNA molecule that is able to specifically interact with a protein or peptide target.

"Inaccessible epitope" means that target epitope modification by the chemical blocking agent is prevented or significantly reduced (e.g. reduced by at least: 50%, 75%, 90%, or 95%), for example, by differential misfolding relative to the wild type polypeptide, by aggregation of misfolded polypeptide or by post-translational modifications of the polypeptide. In some cases, inaccessible epitope is converted to accessible epitope by removing the hindrance (e.g. misfolding or aggregation) that prevents or significantly reduces target epitope modification by the blocking agent. The inaccessible epitope that is converted to accessible epitope may also be called "revealed epitope".

"Detection agent" refers to an agent that binds to epitope and which may be detected, such as antibody specific for prion polypeptide epitopes that can be used to probe the sample containing the polypeptide. The detection agent is used after the polypeptide is unfolded such that the detection preferentially binds the unblocked, unmodified epitopes.

"Disease protein or disease polypeptide" refers to a polypeptide associated with a disease or disorder state where the modular or higher order conformation of the polypeptide differs from the wild type or non-disease conformation and includes mutants, variants and polymorphic versions thereof. A disease protein or disease polypeptide can also be referred to as non-wild type conformation protein or polypeptide. The modular conformation refers to conformational changes in the three dimensional structure of a single protein molecule. The higher order conformation refers to conformational changes in the three dimensional structure of many protein molecules aggregated together. The aggregation can consist of one or more different proteins and can be associated with non-protein molecules. The wildtype and non-wildtype candidate polypeptides including disease proteins or polypeptides also include recombinant proteins, such as cellularly expressed (i.e. bacteria, using baculovirus systems etc.) and in vitro translated polypeptides.

"Wildtype folded conformation" refers to the wild type, folded conformation of protein in a non-disease or non-disorder state.

"Misfolded conformation" refers to the folded conformation of polypeptide in a disease or disorder state where the conformation differs from the wild type conformation. The difference in conformation is as a result of differential folding. The differential folding may cause protein aggregation.

"Wildtype conformation" refers to the conformation of polypeptide in its usual or normal state or in a reference or desired state and can include polypeptide in a non-disease or disorder state.

"Non-wildtype conformation" refers to a conformation of polypeptide that differs from the conformation of the wild type polypeptide and can include a conformation of polypeptide in a disease or disorder, where the conformation differs from the wild type conformation. The difference in conformation may be as a result of differential folding, polypeptide aggregation or differential post-translational modification compared to the wild type polypeptide. In the case of polypeptide aggregation, the aggregation may prevent accessibility of the epitope rather than the changed conformation.

Neurodegenerative diseases, such as Alzheimer's disease (AD), amyotrophic lateral sclerosis (ALS) and Parkinson's disease/Lewy body dementia (PD, LBD) pose major challenges to the aging population and health care system. No specific biochemical test exists for neurodegenerative diseases as a group (1,2). Sporadic AD, ALS, and PD/LBD are all associated with neural accumulation of pathological multimers of misfolded polypeptides (such as fibrils, protofilaments, and amorphous aggregates), including the Abeta fragment of the amyloid precursor protein (APP) in AD; superoxide dismutase-1 (SOD1) in ALS, and alpha-synuclein in PD and LBD (1). As with prion diseases, mutations in genes encoding these aggregation-prone polypeptides are associated with autosomal dominant familial forms of AD, ALS, and PD. The detection of disease-associated misfolded polypeptide aggregates enables specific and sensitive antemortem diagnostic tests for neurodegenerative diseases.

To this end the inventor has invented the "epitope protection assay" (EPA), an innovative technology for detection of aggregated polypeptides in tissues and accessible biological fluids, such as blood and CSF, which serve as "sinks" for the aggregates released from dying neurons. The method optionally consists of:
  reacting a sample with a chemical modifying agent;
  disaggregating and denaturing the treated polypeptides;
  probing the sample with detection agents such as antibodies against specific epitopes blocked by the chemical modifier; and
  detection of agent-bound polypeptides (e.g., by ELISA).

Normal soluble polypeptides in the sample are rendered "invisible" in the assay, because accessible epitopes are not detected by a detecting agent (eg. blocked to antibody recognition), whereas a proportion of polypeptides in aggregates are "protected" from chemical modification by virtue of their interior sequestration, and are still available to be detected by a detecting agent (eg. bind antibody) after disaggregation.

The methods of the invention are useful to diagnose diseases characterized by polypeptide misfolding and/or aggregation such as in the diseases mentioned above or for diseases or disorders characterized by polypeptides with otherwise differentially accessible target epitopes in disease and wild-type protein conformations.

The present inventor has also found that treatment of recombinant mouse prion polypeptide (rmPrP) at low pH in the presence of low concentrations of denaturants causes the polypeptide to acquire increased beta-sheet content, reminiscent of the misfolded disease-associated prion polypeptide isoform, $PrP^{Sc}$. This conversion of rmPrP is associated with increased solvent accessibility of tyrosine side chains[4]. The inventor has found that treatment of normal brain homogenate with acid and denaturants causes PrP to become detergent insoluble (29). In order to probe the surface accessibility of tyrosines and other residues in normal and misfolded $PrP^{C}$, normal and acid-misfolded human brain tissue was treated with the chemical nitrating compound peroxynitrite. Peroxynitrite treatment of brain tissue caused a reduction in the binding of the anti-PrP antibodies 3F4 and 6H4 as measured by immunoblotting, immunoprecipitation and ELISA. Peroxynitrite-induced epitope blocking was more pronounced on normal brain PrP than on misfolded PrP, showing a protective effect of aggregation. Similar findings were observed in normal and scrapie-infected hamster brain, in which 3F4 and 6H4 epitopes of scrapie brain PrP were partially protected from peroxynitrite-induced modification. Immunoprecipitation of peroxynitrite-treated brain with anti-nitrotyrosine antibodies suggests that either PrP is nitrated on tyrosine residues or another polypeptide in proximity to PrP is nitrated and coimmunoprecipitates PrP.

Accordingly, the invention includes a method of determining polypeptide aggregation, including but not limited to $PrP^{Sc}$, comprising:

- reacting a sample with a chemical modifying agent where such agent could be, but is not limited to, peroxynitrite
- disaggregating and/or denaturing the chemically modified sample with heat, detergent, or chaotropic agents; and
- probing with antibodies specific for prion polypeptide epitopes.

The inventor has further shown that the methods of the invention are useful for detecting Alzheimer disease proteins.

In one embodiment, the Alzheimer's disease detection method comprises:

- reacting a sample of polypeptide (the sample typically contains all or part of a disease protein or polypeptide such as amyloid precursor polypeptide or amyloid beta or tau and/or the corresponding wild type polypeptide, and in many cases an abundance of one or the other) with a chemical modifying agent, typically a blocking agent such as peroxynitrite, which modifies exposed epitopes so that they cannot bind to a detection agent;
- disaggregating and/or denaturing the polypeptide in the sample; and
- probing with detection agents, such as an antibody against a target epitope to determine whether the polypeptide prior to disaggregation and/or denaturing, included inaccessible target epitopes.

Abeta containing vascular or plaque filaments are also associated with conditions such as trisomy 21 (Down's syndrome), hereditary cerebral hemorrhage with amyloidosis (HCHWA)-Dutch type, and normal brain aging (Mori, H et al. JBC (1992) 267: 17082-86). Accordingly, in one embodiment detection of Abeta disease protein is prognostic for diseases HCHWA-Dutch type or normal brain aging.

In addition, the methods of the invention can be combined with other diagnostic methods such as magnetic resonance imaging (MRI) or computed tomography (CT) scans to confirm diagnosis.

The methods of the invention are useful to detect protein or polypeptide including target that exists in two or more conformations, where one or more target epitopes are concealed in at least one conformation.

Accordingly, the invention relates to a detection method comprising:
reacting polypeptide with a chemical modifying agent, typically a blocking agent, which is defined to modify exposed epitopes so that they cannot bind to detection agents;
disaggregating and/or denaturing the polypeptide in the sample; and
probing with detection agents, such as antibodies against target epitope to determine whether the polypeptide prior to disaggregation and/or denaturing, included target epitopes inaccessible to the chemical modifying agent.

The result indicates whether the polypeptide includes inaccessible epitopes, which is indicative of the type of polypeptide that is present (i.e. wild type or non-wild type protein).

The invention also includes a method of detecting whether a candidate polypeptide including a target epitope that has been reacted with a blocking agent, is in a wildtype conformation or a non-wildtype conformation, comprising:
modifying the candidate polypeptide to convert any inaccessible target epitope to accessible target epitope; and
contacting the polypeptide with a detection agent that binds selectively to the target epitope that was converted from inaccessible target epitope to accessible target epitope, wherein binding between detection agent and converted target epitope indicates that the candidate polypeptide was in a non-wildtype conformation and wherein lack of binding between the detection agent and the target epitope indicates that the polypeptide was in a wild type conformation.

In another application, the invention also includes a method of detecting intrinsically modified polypeptide, wherein the modification protects target epitope from reacting with the detecting agent, comprising:
contacting the polypeptide with a blocking agent that selectively blocks accessible target epitope, wherein in one of the non-wildtype conformation or the wildtype conformation, the target epitope is accessible and reacts with the blocking agent, and wherein in the other conformation, the target epitope is inaccessible and does not react with the blocking agent;
reacting the sample with an agent that removes the intrinsic modification from the intrinsically modified polypeptide target epitope;
disaggregating and/or denaturing the polypeptide in the sample; and
probing with a detection agent, such as antibodies against the target epitope, to determine whether the candidate polypeptide is an intrinsically modified polypeptide.

Chemical Modifying Agents

The chemical modifying agent of the invention comprises any chemical (including a biological agent) that modifies target epitope residues such that the epitope is rendered invisible by the methods of the invention (ie. not detected by the detecting agent or detection is reduced). For example, peroxynitrite preferentially modifies tyrosine, serine, methionine, histidine and tryptophan as well as cysteine and other amino acids (25, 26). DEPC preferentially modifies histidines (37), and succinic anhydride preferentially modifies residues comprising amines. Epoxides, including conduritol-B-epoxide and 1,2-epoxy-3-(p-nitrophenoxy)propane) are a reactive group used widely for "suicide inhibition" of carboxyl group side chains, such as the catalytic residues of aspartyl proteases (19, 20). Hydrogen peroxide and methylene are also useful. The chemicals may modify the target epitope by oxidizing, nitrating, reducing, or otherwise modifying the epitope. In addition, the epitope may be modified by a chemical modifying agent that is a phosphate group (by phosphorylation), or a gylcosyl group (by gylcosylation), and/or other chemical group that obscures the target epitope.

Accordingly, in one embodiment the chemical modifying agent is chosen from the group peroxynitrite, DEPC, hydrogen peroxide, succinic anhydride, methylene and epoxides (conduritol-B-epoxide and 1,2-epoxy-3-)p-nitrophenoxy) propane and/or related variants thereof.

After reacting with candidate polypeptides, the chemical modifying agent is removed. It is readily apparent to a skilled person that the method steps of the invention recited here involving removing the blocking agent typically involve physically, chemically or otherwise removing the blocking agent away from the candidate polypeptide to prevent further reaction. Removal optionally involves allowing a sufficient time to pass so that the blocking agent is removed from the candidate polypeptide by being consumed or degraded (for example, such that the blocking agent becomes inert or oxidized). Removal optionally involves adding a compound to react with any excess blocking agent to inactivate it. Removal also optionally involves physical filtering of the blocking agent by conventional filtration techniques or centrifugation to separate the candidate polypeptide and blocking agent, or physical binding to a substrate useful for removing the blocking agent, such as by binding of blocking agent or candidate polypeptide to an immobilized substrate in a column.

Removing means preventing further reactions by the blocking agent by, for example, physically or chemically inactivating the blocking agent, taking the blocking agent out of contact with the sample including the candidate polypeptide or allowing a sufficient amount of time to pass for the blocking agent to be consumed or degraded.

Chemical modification of a target epitope leads to obscuration of an epitope to antibody recognition. In one embodiment treatment with a blocking agent such as peroxynitrite leads to destruction of epitopes on monomeric proteins but not epitopes on aggregated proteins such as non-wild type polypeptides or disease proteins.

Pretreatment

The methods of the invention also contemplate pretreatment of the sample to enhance EPA detection. For example if decreased detection of aggregated proteins such as prions in blood or urine is observed, pre-clearing strategies are readily employed to enhance detection with detergents, precipitating agents, and adsorbents such as those typically used in commercial ELISA assays which are known to one skilled in the art. Polypeptide samples may also be pretreated with agents such as detergents or quanidine or heat. Finally samples may be concentrated or precleared by methods such as centrifugation. Accordingly, in one embodiment the samples are pretreated before employing a method of the invention.

Detecting Misfolded or Aggregated Proteins and Polypeptides

The inventor has found a method that detects polypeptides that have target epitopes that are accessible to detection in one conformation and inaccessible in another by modification of inaccessible epitopes by a modifying agent. The inventor has identified several epitopes that are useful as target epitopes in the methods of the invention. Other target epitopes are identified as described below.

Target Epitopes

Target epitopes are identified for polypeptides that exist in two or more conformations wherein epitopes that can be detected by detecting agents such as antibodies, aptamers or peptides, are accessible in one conformation and inaccessible in the other conformation. Where an epitope is found to be blocked from detection by a blocking agent in one conformation of the polypeptide, the epitope is a target epitope. To identify target epitopes, a detection agent such as an antibody is chosen. If the detection agent is an antibody it is preferably a monoclonal antibody although polyclonal antibodies are also usable. The epitope, which can be a linear or non-linear epitope, and which is specifically recognized by the antibody, is optionally a known epitope. A candidate chemical modifying agent such as peroxynitrate is chosen. If the epitope recognized by the detection agent is known, the candidate chemical modifying agent is preferably chosen based on its ability to modify amino acid residues in the target epitope. For example peroxynitrite preferentially modifies tyrosine and histidine residues with some modification of cysteine and other amino acids. Peroxynitrite is optionally chosen as chemical modifying agent if tyrosines and/or histidines are present in the target epitope. Aliquots of a sample comprising wild type polypeptide and aliquots of a sample comprising non-wildtype polypeptide are reacted with increasing concentrations of the chosen chemical modifying agent. Each sample comprises one or more of recombinant polypeptide, cell extracts or tissue samples known to express the polypeptide in either the wild type or non-wild type conformation. Preferably samples of polypeptide have similar concentrations of polypeptide. The non-wildtype conformation polypeptide sample is alternatively obtained by treating a polypeptide in wild type conformation with an agent, such as acid, that induces conversion to a non-wildtype conformation.

Each sample of polypeptide is denatured and/or disaggregated to convert any inaccessible putative target epitope to accessible target epitope. Each sample of polypeptide is then contacted with the chosen detection agent. Detection is performed using techniques known in the art such as ELISA, and Western blotting. The amount of signal generated by the detection agent for sample comprising polypeptide in a wildtype conformation treated with protection agent and for sample comprising polypeptide in a non-wildtype conformation treated with protection agent are compared. A difference in detection at one or more concentrations of chemical modifying agent indicates that the epitope is protected in one conformation and further indicates that the epitope is a target epitope. A difference over a range of chemical modifying agent concentrations indicates that the target epitope is useful for EPA. The process is repeated with different blocking agents and/or detecting agents and target epitopes are identified. One typically standardizes and titrates the blocking agent and to performs experiments using a "universal" chemical modifier such as methylene[24,25], which optionally yields more uniform and complete protection of the target epitope.

Accordingly in one example, a method of identifying a target epitope in a polypeptide that has two or more conformations wherein the target epitope is accessible to detection in one conformation and inaccessible in another conformation comprises:

reacting a sample comprising polypeptide in a wild type conformation and a sample comprising polypeptide in a non-wild type conformation typically with one or more concentrations of a chemical modifying agent;

denaturing and/or disaggregating each sample to convert any inaccessible target epitope to accessible target epitope;

contacting the samples with a detection agent; and comparing the signal generated by the detection agent for samples comprising polypeptide in a wildtype conformation treated with chemical modifying agent and for samples comprising polypeptide in a non-wildtype conformation treated with chemical modifying agent wherein a difference in detection between sample comprising wildtype polypeptide and sample comprising non-wild type sample indicates that the epitope is protected in one conformation and further indicates that the epitope is a target epitope.

ALS-Specific Epitopes

The inventor provides unique "ALS-specific epitopes" presented by or antibody-accessible on monomeric or misfolded forms of SOD1 in monomeric, dimeric or aggregate form, but not on the native homodimeric form of SOD1. The following 2 epitopes have been identified by the inventor as ALS-specific epitopes:

```
DLGKGGNEESTKTGNAGS;      (SEQ ID NO: 1)
and

NPLSRKHGGPKDEE.          (SEQ ID NO: 2)
```

A person skilled in the art will appreciate that the ALS-specific epitope can be all or part of the above sequences. The term "part of" as used herein refers to the sequence that retains the epitope activity for eliciting an immune response in an animal. The invention also includes variants of the above sequences.

The term "variant" as used herein includes modifications or chemical equivalents of the amino acid and nucleotide sequences of the present invention that perform substantially the same function as the proteins or nucleic acid molecules of the invention in substantially the same way. For example, variants of proteins of the invention include, without limitation, conservative amino acid substitutions. Variants of proteins of the invention also include additions and deletions to the proteins of the invention. In addition, variant peptides and variant nucleotide sequences include analogs and derivatives thereof.

A "conservative amino acid substitution", as used herein, is one in which one amino acid residue is replaced with another amino acid residue without abolishing the peptide's desired properties.

The term "derivative of a peptide" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides.

Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

The peptides constituting these epitopes can further comprise additional amino acid residues particularly at the N- and C-terminal flanks thereof, which may be useful in conjugating the epitope with an agent useful for instance in eliciting an immune response, or an agent serving as a tag useful in the production of the epitope or to monitor its presence. For instance, the epitope may further comprise an N-terminal Cys residue to assist with coupling to KLH or the like. The epitope may further comprise a linker effective to couple the epitope tandemly to another copy of the same or a different epitope. Alternatively, the epitope may further comprise a polyhistidine or Flag tag, In another embodiment, the epitopes may comprise additional amino acids that enhance the immunogenecity or solubility of the epitope. In one embodiment, the additional amino acids number from 1 to about 10, preferably 1 to 8, more preferably 1 to 5. Importantly the additional residues do not materially affect the conformation of the epitope.

In one embodiment of the invention, the variant amino acid sequence has at least 70% sequence identity, preferably at least 80% sequence identity, more preferably at least 90% sequence identity to the above sequences (SEQ ID NO:1 and SEQ ID NO:2). The term "sequence identity" as used herein refers to the percentage of sequence identity between two polypeptide sequences. In order to determine the percentage of identity between two polypeptide sequences, the amino acid sequences of such two sequences are aligned, preferably using the Clustal W algorithm (Thompson, J D, Higgins D G, Gibson T J, 1994, Nucleic Acids Res. 22 (22): 4673-4680), together with BLOSUM 62 scoring matrix (Henikoff S, and Henikoff J. G., 1992, Proc. Natl. Acad. Sci. USA 89: 10915-10919) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Other methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990:215:403).

A person skilled in the art will appreciate that there may be other ALS-specific epitopes. For example, other disease specific epitopes may be identified using the epitope protection assay described in herein. In another example, other disease specific epitopes may be identified using the method disclosed in Khare et al. (Proteins: Structure, Function and Bioinformatics (2005) 61:617-632). Furthermore, useful epitopes can be identified as those presenting uniquely in SOD1 that is acidified, or otherwise treated to induce adoption of a monomeric or misfolded conformation, relative to a pH neutral control SOD1.

Conditions for EPA

Titration experiments with peroxynitrite, hydrogen peroxide and methylene (based on UV light photolysis of the precursor diazirine) or other modifying agents, are useful to improve conditions for epitope protection.

Samples known to contain polypeptides in two or more conformations, including disease proteins, are optionally reacted using immunoblotting and ELISA. In each case, samples are prepared and optionally mixed with increasing concentrations of the modifying agent and processed, for example, by immunoblotting, ELISA and/or time resolved fluorescence. This defines the type and concentration of chemical agent allowing the maximal distinction between monomeric and aggregated proteins including disease proteins. Additional informative experiments can involve using recombinant disease (non-wild type) protein (such as acid treated prion proteins or mutant p53 proteins and other protein listed in this application) and normal (wild type) protein in place of samples containing disease proteins.

In some cases, disease proteins may have different properties for chemical modification than do recombinant disease proteins, and disease proteins in one sample type (such as brain tissue) may display different chemical modification properties than disease proteins circulating in blood, or detectable in urine. One of skill in the art shall readily identify the optimal conditions for endogenous prions using known techniques.

The EPA achieves superior commercial utility by detecting disease proteins in biological tissues and fluids for which no present technology exists. Some disease proteins are in very low abundance. For example prions are in very low abundance (10-100 prions/mL by bioassay), and protease-resistant PrP in urine is only intermittently/sporadically detectable by precipitation of large fluid volumes. Also, any prospective blood test must contend with high concentrations of wildtype protein (i.e. for $PrP^C$ (typically $10^6$-fold more than $PrP^{Sc}$)) and "blocking" by heterologous plasma proteins. Using the optimized chemical modification regimen and the DELFIA-TRF system, the sensitivity thresholds for EPA in blood and urine are optionally determined using:

1. Animal and human plasma and urine "spiked" with a titration of disease protein;
2. Plasma and urine from model disease animals expressing a disease protein.

Biological fluids clinically accessible by non-invasive routes provide a substrate for a practical antemortem test for diagnosis and screening of diseases involving aggregated disease proteins in humans and animals. The methods of this invention are also useful in post-mortem testing. One of skill in the art readily determines whether EPA with "disease protein spike" titration in normal blood and urine reveals similar DELFIA-TRF signals to the same disease protein titration in buffer, showing that the EPA is not affected by "blocking factors" in these biological fluids. Preferential "blocking" of disease protein by heterologous proteins may actually enhance epitope protection to chemical modifying agents. If decreased detection of disease protein in blood or urine is observed, pre-clearing strategies are readily employed to enhance disease protein detection, for example, with detergents, precipitating agents, and adsorbents typically used in commercial ELISA assays which are known to one skilled in the art.

In one embodiment, the methods of the invention involve the detection of target epitopes in misfolded or aggregated polypeptides. In another embodiment, the invention provides a method for improving or optimizing the detection of polypeptides that can exist in 2 or more conformations. In another embodiment the detection of misfolded and/or aggregated polypeptides is indicative of disease (disease proteins). In another embodiment, polypeptides are detected using detection agents such as antibodies, aptamers or peptides that specifically bind to epitopes of polypeptides that can be chemically modified. In another embodiment these polypeptides are disease proteins. Antibodies to candidate protein epitopes are commercially available antibodies or are readily prepared by a person skilled in the art and include antibody fragments, and single chain antibodies. All the aforementioned methods are readily implemented using steps described in this application.

Antibodies

The invention contemplates the use of known antibodies as the binding agent including biotin-3F4 and 3F4 and 6H4 which recognize prion disease proteins. 3F4 reacts against the MKHV (SEQ ID NO:3) epitope and 6H4 reacts against the DYEDRYYRE (SEQ ID NO:4) epitope. Additionally, 6E10 which recognizes Abeta, reacts against the EFRHDS (SEQ ID NO:5) epitope (residues 3-8).

Other antibodies and the epitopes recognized (if known) which are optionally used with the methods of the invention are listed in the table below.

Thus, the invention includes compositions for eliciting an immune response in an animal comprising an effective amount of an isolated ALS-specific epitope in admixture with a suitable diluent or carrier, wherein the ALS-specific epitope comprises an isolated peptide selected from the group consisting of:

```
DLGKGGNEESTKTGNAGS;        (SEQ ID NO: 1)
and

NPLSRKHGGPKDEE.            (SEQ ID NO: 2)
```

The term "animal" as used herein includes all members of the animal kingdom including mammals, and preferably includes animals capable of making antibodies.

Immunogenicity can be significantly improved if the immunizing agent(s) (e.g. isolated ALS-specific epitope) and/or composition is, regardless of administration format, co-immunized with an adjuvant. Commonly, adjuvants are used as in 0.05 to 1.0 percent solution in phosphate buffered saline. Adjuvants enhance the immunogenicity of an immunogen but are not necessarily immunogenic themselves. Adjuvants may act by retaining the immunogen locally near

TABLE

Antibodies useful to detect disease proteins

| Protein | Antibody | Mono/Poly | Epitope | Company |
|---|---|---|---|---|
| Abeta | 4G8 | Monoclonal | Within aa18-22 of human Abeta | Signet |
| | 6E10 | Monoclonal | Within aa3-8 of human Abeta | Signet |
| | ab2539 | Polyclonal | NA | Abcam |
| | Abeta-NT | Polyclonal | NA | QED Bioscience |
| | DE2B4 | Monoclonal | Within aa1-17 of human Abeta | Acris antibodies |
| | NBA-104E | Monoclonal | Within aa1-16 of human Abeta | Stressgen |
| Alpha-synuclein | 4D6 | Monoclonal | Unknown | Acris antibodies |
| | ab6162 | Polyclonal | NA | Abcam |
| | LB509 | Monoclonal | Unknown | Zymed |
| | Syn-1 | Monoclonal | Within aa91-99 of human a-syn | BD Biosciences |
| | Syn-204 | Monoclonal | Within aa87-110 of human a-syn | Lab Vision |
| | Syn-211 | Monoclonal | Within aa121-125 of human a-syn | Lab Vision |
| Tau | Mouse Anti-Tau-1 | Monoclonal | Within aa95-108 of human tau | Biomeda |
| | Mouse Anti-Tau-2 | Monoclonal | Unknown | Stressgen |
| | T14 | Monoclonal | Within aa141-178 of human tau | Zymed |
| | T46 | Monoclonal | Within aa404-441 of human tau | Zymed |
| | Tau-2 | Monoclonal | Unknown | Acris antibodies |
| | Tau-5 (ab3931) | Monoclonal | Unknown | Abcam |
| SOD1 | Mouse SOD1 | Monoclonal | Unknown | Sigma-aldrich |
| | Rabbit SOD1 | Polyclonal | Unknown | Stressgen |
| | Rat SOD1 | Polyclonal | Unknown | Stressgen |
| | Sheep SOD1 | Polyclonal | Unknown | OxisResearch |

The invention also includes isolated antibodies to the novel ALS-specific epitopes disclosed herein, and compositions and methods for making the antibodies. For example these novel epitopes can be used to elicit an immune response in an animal, for example to make antibodies specific for the epitope. The phrase "eliciting an immune response" is defined as initiating, triggering, causing, enhancing, improving or augmenting any response of the immune system, for example, of either a humoral or cell-mediated nature. The initiation or enhancement of an immune response can be assessed using assays known to those skilled in the art including, but not limited to, antibody assays (for example ELISA assays), antigen specific cytotoxicity assays and the production of cytokines (for example ELISPOT assays).

the site of administration to produce a depot effect facilitating a slow, sustained release of immunogen to cells of the immune system. Adjuvants can also attract cells of the immune system to an immunogen depot and stimulate such cells to elicit immune responses. As such, embodiments of this invention encompass compositions further comprising adjuvants.

Adjuvants have been used for many years to improve the host immune responses to, for example, vaccines. Intrinsic adjuvants (such as lipopolysaccharides) normally are the components of killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established. Notwithstanding, it does have limitations. For example, alum is ineffective for influenza vaccination and inconsistently elicits a cell mediated immune response with other immunogens. The antibodies elicited by alum-adjuvanted antigens are mainly of the IgG1 isotype in the mouse, which may not be optimal for protection by some vaccinal agents.

A wide range of extrinsic adjuvants can provoke potent immune responses to immunogens. These include saponins complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

In one aspect of this invention, adjuvants useful in any of the embodiments of the invention described herein are as follows. Adjuvants for parenteral immunization include aluminum compounds (such as aluminum hydroxide, aluminum phosphate, and aluminum hydroxy phosphate). The antigen can be precipitated with, or adsorbed onto, the aluminum compound according to standard protocols. Other adjuvants such as RIBI (ImmunoChem, Hamilton, Mont.) can also be used in parenteral administration.

Adjuvants for mucosal immunization include bacterial toxins (e.g., the cholera toxin (CT), the *E. coli* heat-labile toxin (LT), the *Clostridium difficile* toxin A and the pertussis toxin (PT), or combinations, subunits, toxoids, or mutants thereof). For example, a purified preparation of native cholera toxin subunit B (CTB) can be of use. Fragments, homologs, derivatives, and fusion to any of these toxins are also suitable, provided that they retain adjuvant activity. Preferably, a mutant having reduced toxicity is used. Suitable mutants have been described (e.g., in WO 95/17211 (Arg-7-Lys CT mutant), WO 96/6627 (Arg-192-Gly LT mutant), and WO 95/34323 (Arg-9-Lys and Glu-129-Gly PT mutant)). Additional LT mutants that can be used in the methods and compositions of the invention include, for example Ser-63-Lys, Ala-69-Gly, Glu-110-Asp, and Glu-112-Asp mutants. Other adjuvants (such as a bacterial monophosphoryl lipid A (MPLA) of various sources (e.g., *E. coli, Salmonella minnesota, Salmonella typhimurium*, or *Shigella flexneri*, saponins, or polylactide glycolide (PLGA) microspheres) can also be used in mucosal administration.

Adjuvants useful for both mucosal and parenteral immunization include polyphosphazene (for example, WO 95/2415), DC-chol (3 b-(N-(N',N'-dimethyl aminomethane)-carbamoyl) cholesterol (for example, U.S. Pat. No. 5,283,185 and WO 96/14831) and QS-21 (for example, WO 88/9336).

The immunogenicity or effectiveness of the composition to treat amyotrophic lateral sclerosis or elicit an immune response can also be enhanced by conjugating the isolated ALS-specific epitope to a molecule that enhances the immunogenicity of the epitope. For example, the ALS-specific epitope can be conjugated to keyhole limpet hemocyanin (KLH). KLH is a respiratory protein found in mollusks. Its large size makes it very immunogenic, and the large number of lysine residues available for conjugation make it very useful to attach to an protein, such as an isolated ALS-specific epitope.

The ALS-specific epitopes may be prepared using a variety of methods known to one skilled in the art. Accordingly, ALS-specific epitopes may be prepared by chemical synthesis using techniques well known in the chemistry of proteins such as solid phase synthesis (Merrifield, J. Am. Chem. Assoc. 85:2149-2154 (1964)) or synthesis in homogenous solution (Houbenweyl, Methods of Organic Chemistry, ed. E. Wansch, Vol. 15, pts. I and II, Thieme, Stuttgart (1987)).

The ALS-specific epitopes may also be produced by recombinant DNA technology. To prepare the ALS-specific epitopes by recombinant DNA techniques, a DNA sequence encoding the ALS-specific epitopes must be prepared. Consequently, the present invention also includes the use of purified and isolated nucleic acids comprising a nucleotide sequence coding for ALS-specific epitopes to elicit an immune response.

In one embodiment the nucleic acid sequence encoding the ALS-specific epitopes is incorporated into an expression vector adapted for transfection or transformation of a host cell. The nucleic acid molecules may be incorporated in a known manner into an appropriate expression vector which ensures expression of the protein. Possible expression vectors include but are not limited to cosmids, plasmids, or modified viruses (e.g. replication defective retroviruses, adenoviruses and adeno-associated viruses). The vector should be compatible with the host cell used. The expression vectors are "suitable for transformation of a host cell", which means that the expression vectors contain a nucleic acid molecule encoding the ALS-specific epitopes and regulatory sequences selected on the basis of the host cells to be used for expression, which is operatively linked to the nucleic acid molecule. "Operatively linked" is intended to mean that the nucleic acid is linked to regulatory sequences in a manner which allows expression of the nucleic acid.

Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. 1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors may also contain a marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

Recombinant expression vectors can be introduced into host cells to produce a transformant host cell. The term "transformant host cell" is intended to include prokaryotic and eukaryotic cells which have been transformed or transfected with a recombinant expression vector encoding the ALS-specific epitopes. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

More particularly, bacterial host cells suitable for carrying out the present invention include *E. coli, B. subtilis, Salmonella typhimurium*, and various species within the genus *Pseudomonas, Streptomyces*, and *Staphylococcus*, as well as many other bacterial species well known to one of ordinary skill in the art. Suitable bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., Nature 275:615 (1978)), the trp promoter (Nichols and Yanofsky, Meth. in Enzymology 101:155, 1983) and the tac promoter (Russell et al., Gene 20: 231, 1982). Representative selectable markers include various antibiotic resistance markers such as the kanamycin or ampicillin resistance genes. Suitable expression vectors include but are not limited to bacteriophages such as lambda derivatives or plasmids such as pBR322 (see Bolivar et al., Gene 2:9 S, (1977)), the pUC plasmids pUC18, pUC19, pUC118, pUC119 (see Messing, Meth in Enzymology 101:20-77, 1983 and Vieira and Messing, Gene 19:259-268 (1982)), and pNH8A, pNH16a, pNH18a, and Bluescript M13 (Stratagene, La Jolla, Calif.). Typical fusion expression vectors which may be used are discussed above, e.g. pGEX (Amrad Corp., Melbourne, Australia), pMAL (New England Biolabs, Beverly, Mass.) and pRIT5 (Pharmacia, Piscataway, N.J.). Examples of inducible non-fusion expression vectors include pTrc (Amann et al., Gene 69:301-315 (1988)) and pET 11d (Studier et al., Gene Expression Technology: Methods in Enzymology 185, Academic Press, San Diego, Calif., 60-89 (1990)).

Yeast and fungi host cells suitable for carrying out the present invention include, but are not limited to *Saccharomyces cerevisiae, Schizosaccharomyces pombe*, the genera *Pichia* or *Kluyveromyces* and various species of the genus *Aspergillus*. Examples of vectors for expression in yeast *S. cerivisiae* include pYepSec1 (Baldari. et al., Embo J. 6:229-234 (1987)), pMFa (Kurjan and Herskowitz, Cell 30:933-943 (1982)), pJRY88 (Schultz et al., Gene 54:113-123 (1987)), and pYES2 (Invitrogen Corporation, San Diego, Calif.). Protocols for the transformation of yeast and fungi are well known to those of ordinary skill in the art (see Hinnen et al., Proc. Natl. Acad. Sci. USA 75:1929 (1978); Itoh et al., J. Bacteriology 153:163 (1983), and Cullen et al. (Bio/Technology 5:369 (1987)).

Mammalian cells suitable for carrying out the present invention include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)) and pMT2PC (Kaufman et al., EMBO J. 6:187-195 (1987)).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., J. Biosci (Bangalore) 11:47-58 (1987), which reviews the use of *Agrobacterium rhizogenes* vectors; see also Zambryski et al., Genetic Engineering, Principles and Methods, Hollaender and Setlow (eds.), Vol. VI, pp. 253-278, Plenum Press, New York (1984), which describes the use of expression vectors for plant cells, including, among others, pAS2022, pAS2023, and pAS2034).

Insect cells suitable for carrying out the present invention include cells and cell lines from *Bombyx* or *Spodotera* species. Baculovirus vectors available for expression of proteins in cultured insect cells (SF 9 cells) include the pAc series (Smith et al., Mol. Cell. Biol. 3:2156-2165 (1983)) and the pVL series (Lucklow, V. A., and Summers, M. D., Virology 170:31-39 (1989)). Some baculovirus-insect cell expression systems suitable for expression of recombinant proteins are described in PCT/US/02442.

The recombinant expression vectors containing the nucleotide sequences encoding the ALS-specific epitopes may also contain genes which encode a fusion moiety (i.e. a "fusion protein") which provides increased expression of the recombinant peptide; increased solubility of the recombinant peptide; and aid in the purification of the target recombinant peptide by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein Another aspect of the invention is a composition for eliciting an immune response in an animal comprising an effective amount of a nucleic acid encoding an isolated ALS-specific epitope in admixture with a suitable diluent or carrier, wherein the ALS-specific epitope comprises an isolated peptide selected from the group consisting of:

```
DLGKGGNEESTKTGNAGS;     (SEQ ID NO: 1)
and

NPLSRKHGGPKDEE.        (SEQ ID NO: 2)
```

In embodiments, nucleic acids encoding the misfolded SOD1-specific epitopes include the following RNA molecules, synonymous codon equivalents thereof, and their DNA counterparts:

```
                                        (SEQ ID NO: 1)
For DLGKGGNEESTKTGNAGS;

(SEQ ID NO: 6)
GAUUUAGGUAAAGGUGGUAAUGAAGAAAGUACUAAAACUGGUAAUGCUGG

UAGU (SEQ ID NO: 2)
For NPLSRKHGGPKDEE;

(SEQ ID NO: 7)
AAUCCUUUAAGUCGUAAACACGGAGGACCGAAGGACGAGGAG.
```

A person skilled in the art will appreciate that there are several modes of administration available when using a composition containing a nucleic acid molecule encoding an isolated ALS-specific epitope. The recombinant molecules described above may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage. The nucleic acid molecules of the invention may also be applied extracellularly such as by direct injection into cells.

Antibodies to disease protein epitopes, such as the ALS-specific epitopes, are prepared using techniques known in the art. For example, by using a peptide of a disease protein including a putative target epitope, polyclonal antisera or monoclonal antibodies are made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the protein or peptide is administered in the presence of adjuvant. The progress of immunization can be monitored by detection of antibody titers in plasma or serum. Standard ELISA or other immunoassay procedures are optionally used with the immunogen as antigen to assess the levels of antibodies. Following immunization, antisera can be obtained and, if desired, polyclonal antibodies isolated from the sera.

To produce monoclonal antibodies, antibody producing cells (lymphocytes) are optionally harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated.

Chimeric antibody derivatives, i.e., antibody molecules that combine a non-human animal variable region and a human constant region are also contemplated within the scope of the invention. Chimeric antibody molecules include, for example, the antigen binding domain from an antibody of a mouse, rat, or other species, with human constant regions. Conventional methods used to make chimeric antibodies containing the immunoglobulin variable region which recognizes disease protein epitopes of the invention (See, for example, Morrison et al., Proc. Natl. Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Specific antibodies, or antibody fragments, such as, but not limited to, single-chain Fv monoclonal antibodies reactive against disease protein epitopes are readily generated by screening expression libraries encoding immunoglobulin genes, or portions thereof, expressed in bacteria with peptides produced from the nucleic acid molecules of disease proteins. For example, complete Fab fragments, VH regions and FV regions are expressed in bacteria using phage expression libraries (See for example Ward et al., Nature 341, 544-546: (1989); Huse et al., Science 246, 1275-1281 (1989); and McCafferty et al. Nature 348, 552-554 (1990)). Alternatively, a SCID-hu mouse, for example the model developed by Genpharm, is used to produce antibodies or fragments thereof.

Antibodies specifically reactive with disease protein epitopes, or derivatives, such as enzyme conjugates or labeled derivatives, are useful to detect disease protein epitopes in various samples (e.g. biological materials). They are useful as diagnostic or prognostic reagents and are readily used to detect abnormalities in the level of protein expression, or abnormalities in the structure, and/or temporal, tissue, cellular, or subcellular location of disease protein epitopes. In vitro immunoassays are also useful to assess or monitor the efficacy of particular therapies. The antibodies of the invention may also be used in vitro to determine the level of expression of a gene of a polypeptide that exists in two or more conformations such as a disease protein in cells genetically engineered to produce the disease protein.

Accordingly, the invention includes isolated antibodies made using the compositions of the invention and antibodies specific for an ALS-specific epitope, wherein the ALS-specific epitope comprises an isolated peptide selected from the group consisting of:

```
DLGKGGNEESTKTGNAGS;       (SEQ ID NO: 1)
and

NPLSRKHGGPKDEE.           (SEQ ID NO: 2)
```

The antibodies are useful in any known immunoassays which rely on the binding interaction between an antigenic determinant of the disease protein epitopes and the antibodies. Examples of such assays are radioimmunoassays, enzyme immunoassays (e.g. ELISA including Sandwich ELISA), immunofluorescence, immunoprecipitation, latex agglutination, hemagglutination, and histochemical tests. The antibodies are useful to detect and quantify the disease protein in a sample in order to determine its role and to diagnose the disease caused by the disease protein.

In particular, the antibodies of the invention are useful in immunohistochemical analyses, for example, at the cellular and subcellular level, to detect a disease protein, to localize it to particular cells and tissues, and to specific subcellular locations, and to quantitate the level of expression.

Cytochemical techniques known in the art for localizing antigens using light and electron microscopy to detect polypeptides such as disease proteins. Generally, an antibody of the invention is optionally labeled with a detectable substance and the recognized polypeptide is localised in tissues and cells based upon the presence of the detectable substance. Examples of detectable substances include, but are not limited to, the following: radioisotopes (e.g., $^3$H, $^{14}$C, $^{35}$S, $^{32}$P, $^{123}$I, $^{125}$I, $^{131}$I), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or colorimetric methods), predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualized by electron microscopy.

The antibody or sample may be immobilized on a carrier or solid support which is capable of immobilizing cells, antibodies etc. For example, the carrier or support may be nitrocellulose, or glass, polyacrylamides, gabbros, and magnetite. The support material may have any possible configuration including spherical (e.g. bead), cylindrical (e.g. inside surface of a test tube or well, or the external surface of a rod), or flat (e.g. sheet, test strip). Indirect methods may also be employed in which the primary antigen-antibody reaction is amplified by the introduction of a second antibody, having specificity for the antibody reactive against disease protein epitopes. By way of example, if the antibody having specificity against a polypeptide epitope such as a disease protein epitope is a rabbit IgG antibody, the second antibody may be goat anti-rabbit gamma-globulin labeled with a detectable substance as described herein.

Where a radioactive label is used as a detectable substance, disease proteins may be localized by autoradiography. The results of autoradiography may be quantitated by determining the density of particles in the autoradiographs by various optical methods, or by counting the grains.

One embodiment of the invention is a method of detecting or diagnosing amyotrophic lateral sclerosis in a subject comprising the steps of:

(a) contacting a test sample of said subject with any one of the antibodies of the invention, wherein the antibody binds to an ALS-specific epitope to produce an antibody-antigen complex;

(b) measuring the amount of the antibody-antigen complex in the test sample; and (c) comparing the amount of antibody-antigen complex in the test sample to a control wherein a difference in the amount of antibody-antigen complex in the test sample as compared to the control is indicative of amyotrophic lateral sclerosis.

The phrase "detecting or monitoring amyotrophic lateral sclerosis" refers to a method or process of determining if a subject has or does not have amyotrophic lateral sclerosis or the extent of the amyotrophic lateral sclerosis. In addition, the antibodies of the invention can be used to detect or monitor the appearance and progression of SOD1 aggregation, and hence progression of the disease.

The term "control" as used herein refers to a sample from a subject or a group of subjects who are either known as having amyotrophic lateral sclerosis or not having amyotrophic lateral sclerosis. A person skilled in the art will appreciate that the difference in the amount of antibody-antigen complex will vary depending on the control. For example, if the control is known to have amyotrophic lateral sclerosis, then less measurable antibody-antigen complex in the test sample as compared to the control indicates that the subject does not have amyotrophic lateral sclerosis or that they have less of an extent of amyotrophic lateral sclerosis. If the control is known to have amyotrophic lateral sclerosis, then equal or greater measurable antibody-antigen complex in the test sample as compared to the control indicates that the subject has amyotrophic lateral sclerosis. If the control is known not to have amyotrophic lateral sclerosis, then less or equal measurable antibody-antigen complex in the test sample as compared to the control indicates that the subject does not have amyotrophic lateral sclerosis. If the control is known not to have amyotrophic lateral sclerosis, then greater measurable antibody-antigen complex in the test sample as compared to the control indicates that the subject has amyotrophic lateral sclerosis.

The term "sample" as used herein refers to any fluid, cell or tissue sample from a subject which can be assayed for an ALS-specific epitope, preferably monomeric or misfolded SOD1. In one embodiment, the sample comprises, without limitation, cerebrospinal fluid, plasma, blood serum, whole blood, spinal cord tissue, brain cells, motor neurons, a portion of the dorsal horn, or peripheral blood cells, such as erythrocytes, mononuclear cells, lymphocytes, monocytes and granulocytes.

In one embodiment of the invention, the antibodies are used to determine if monomeric or misfolded SOD1 is present in the sample. In another embodiment, the antibodies are labeled with a detectable marker.

In another embodiment, the epitopes are used to monitor the appearance and titre of antibodies introduced into or raised within a recipient. In this embodiment, a patient sample is mixed with the epitope, and preferably a labeled epitope, and the presence or quantity of bound antibody is determined.

Aptamers

Aptamers are also useful in the methods of the invention to detect polypeptides such as disease proteins. Aptamers are macromolecules that can recognize targets such as proteins with high specificity and sensitivity.

Nucleic acid aptamers are small molecules isolated from combinatorial libraries by a procedure named systemic evolution of ligands by exponential enrichment (SELEX) (reviewed in Cerchia L et al, FEBS Letters 528 (2002) 12-12). Using this technology aptamers that bind proteins with high target specificity and selectivity can be identified. The affinities can be comparable to antibody antigen interactions. Discrimination between native and denatured protein has been shown (Bianchini et al. Immunol Methods (2001) 252:191-97) making aptamers useful detection agents for the methods of the invention.

Peptide aptamers, also known as paptamers, thioredoxin-insert proteins or pertubagens are artificial proteins where an inserted peptide is expressed on a solvent exposed surface of a structurally stable protein which functions as a scaffold (Crawford M. et al. Brief Funct Genomic Proteomic. 2003 April; 2:72-9). Peptide aptamers can function similarly to antibodies and have dissociation constants that are comparable to, and sometimes better than, antibodies. They can be used to probe immobilized proteins on nitrocellulose (Crawford M. et al. Brief Funct Genomic Proteomic. 2003 April; 2:72-9). Peptide aptamers have been shown to exhibit different affinities for small changes such as single amino acid differences making them useful for the detection of polypeptides that exist in two or more conformations such as disease proteins that exhibit different folding or aggregation conformations.

Accordingly, in one embodiment of the invention, nucleic acid and/or peptide aptamers are used with the methods of the invention to distinguish between wild-type and disease conformation proteins. In one embodiment the disease protein is a prion protein. In another embodiment the disease protein is amyloid-beta. In another embodiment the disease protein is tau protein. In another embodiment the disease protein is alpha-synuclein. In another embodiment the disease protein is SOD-1.

Denaturing and Disaggregation

In the methods, the polypeptide is optionally modified by denaturing the polypeptide, for example with heat, detergent and/or chaotropic agents. The polypeptide is optionally modified by treatment with a disaggregation agent to disaggregate the polypeptide from other polypeptides of the same type, and from other molecules, wherein the disaggregation agent is optionally selected from at least one of the group consisting of chaotropic agents, detergent and heat. Chaotropic agents can include but are not limited to such as guanidine salts, urea, and thiourea.

The inventor has shown that treating proteins with guanidine hydrochloride increases the amount of protected protein detectable.

Combining disaggregation methods can result in optimised disaggregation. For example boiling samples in sodium dodecyl sulfate (SDS; also known as sodium lauryl sulfate) loading buffer can increase solubilization of polypeptides such as disease proteins, increasing the epitopes available for interacting with the detecting agent. For example, boiling samples in SDS loading buffer results in enhanced solubilization, and allows detection of protected epitopes by sandwich ELISA. The sandwich ELISA assay system is able to identify aggregated disease protein in tissue homogenate samples if the samples are boiled in SDS loading buffer after peroxynitrite treatment. At peroxynitrite concentrations greater than 8 mM, there is 2.5-3× as much PrP detected in the acid treated sample as compared to the mock treated sample. Accordingly, in one embodiment the sample is boiled in SDS loading after treatment with modifying agent and before detection with a detecting agent such as an antibody.

Time Resolved Fluorescence (TRF) Two Point ELISA and Dissociation Enhanced Lanthanide FluoroImmunoassay (DELFIA)

As previously mentioned ELISA techniques can be employed by the methods of the invention. Time resolved flouresence two-point ELISA employing Dissociation Enhanced Lanthanide FluoroImmunassay (DELFIA) technology is 1000 fold more sensitive than conventional ELISA techniques and can be used with the methods of the invention to detect polypeptides aggregated in vitro, in neural tissue of transgenic mouse models of neurodegeneration, and in human AD, ALS, PD and LBD patient brain samples.

The DELFIA assay uses a chelated lanthanide-labeled tracer, such as europium (Eu) and time-resolved fluorescence (TRF) to measure output signal (33). The benefit of lanthanide chelates is that their fluorescence is intense and lasts up to 200,000 times longer than conventional fluorophores, allowing signal capture after non-specific interfering fluorescence has faded (particularly critical for biological samples, which may possess considerable intrinsic fluorescence, the emission of which is comparatively short-lived). DELFIA-based systems can measure as little as 100 fmol/well of Eu (33).

In one embodiment of the invention, a chemical modifying agent and antibody are employed in a sensitive capture-detection "sandwich" 96-well plate DELFIA TRF system in the detection of aggregated disease specific proteins described herein, such as Abeta, tau, SOD1, huntingtin alpha-synuclein, islet amyloid polypeptide, resistin and p53.

A two-point EPA increases the specificity for detection of proteins sequestered in aggregates of a clinical sample. In one embodiment, two or more chemically modifiable epitopes are present in each test polypeptide, which would increase the specificity of diagnostic tests employing this technology (e.g., use in two-point ELISA). In one embodiment, the chemically modifiable epitopes are modified by the same chemical. In another embodiment, the epitopes are modified by one of two or more different chemicals. The modified epitopes may be recognized by the same antibody or they may be recognized by two or more different antibodies. For clinical and commercial use, EPA must be sensitive and specific for polypeptides aggregated in vitro and in vivo. With optimal antibodies and chemical modifying regimens, and the DELFIA-TRF system EPA can detect $10^5$-$10^6$ molecules of soluble polypeptides This may correspond to a single polypeptide aggregate, if these aggregates are of similar size to prion protein aggregates in disease (35, 36).

Accordingly in one embodiment, the DELFIA-TRF system EPA can be used to identify disease proteins that are in very low abundance, as low as a single polypeptide aggregate.

Diagnostic and Screening Applications

Effective, efficient and inexpensive diagnostic and screening strategies for antemortem diagnosis of human neurodegenerative diseases are urgently needed, given the aging population and continued financial pressure on the health care system. EPA will achieve clinical utility by detecting polypeptide aggregates in relevant and accessible biological tissues and fluids, for which no present technology exists. In one embodiment the methods of the invention are used to diagnose individuals who have a disease protein related disease. In one embodiment, the invention is used to diagnose individuals who have a neurodegenerative disease. In another embodiment, the invention is used to diagnose individuals who have a neurodegenerative disease selected from the group comprising prion related diseases, AD, HD, ALS and PD. In a further embodiment, the methods of the invention are used post-mortem to determine if the individual had a disease protein related disease.

The methods of the invention are used to detect whether a human has a disease protein related disease. In another embodiment, the methods are used to detect if a non-human animal has a disease protein related disease. In a further embodiment the non-human animal is one of the group comprising cattle, sheep and cervids. In another embodiment, the methods of the invention are used to detect if livestock has a disease protein related disease.

In one embodiment the methods of the invention are used to detect disease proteins in biological specimens. The biological specimens may comprise biological fluids, such as CSF, serum, blood, tears, peritoneal exudates, or urine, or tissue samples such as biopsies or brain tissue. The samples in one embodiment are antemortem samples. In another embodiment they are postmortem samples.

The methods of the invention are useful to quantify detection of soluble form of disease related proteins such as Abeta, tau, SOD1 huntingtin, alpha-synuclein, islet amyloid polypeptide, resistin and p53 protein.

In another embodiment, EPA is used to determine the sensitivity and specificity of aggregate detection in homogenates from CRND8 (human mutant APP) mouse brain and CSF (34) and G93A human mutant SOD1 transgenic mice (13).

In another embodiment the invention is used to determine the sensitivity and specificity of aggregate detection in homogenates from normal (treated and untreated at low pH) and diseased frozen human brain (AD, ALS, PD, LBD).

The methods of the invention are used in one embodiment to ensure preparations derived from mammalian blood or tissues or involving processes where mammalian blood or tissues come into contact with preparations, are free of disease proteins. In one embodiment the preparation is a pharmaceutical product. In another embodiment the preparation is a vaccine. In a further embodiment, the preparation is a cosmetic. In one embodiment, the preparations are tested for prion proteins. In another embodiment, the preparations are tested for amyloid-beta. In another embodiment, the preparations are tested for tau protein. In another embodiment, the preparations are tested for alpha-synuclein. In a further embodiment, the preparations are tested for SOD-1.

In another embodiment, the methods of the invention are used to screen blood, and blood products (eg. blood fractions such as blood plasma or compounds isolated or manufactured from blood) used for transfusions or other medical procedures for disease proteins. In another embodiment, the invention is used to screen organ transplants for disease proteins. In one embodiment, the preparations are screened for prion proteins. In another embodiment, the preparations are screened for amyloid-beta. In one embodiment, the preparations are screened for tau protein. In another one embodiment, the preparations are screened for alpha-synuclein. In a further embodiment, the preparations are screened for SOD-1.

The invention is also useful for ensuring that food sources are free of disease proteins. In another embodiment the methods of the invention are used to test edible products derived from mammals such as meats and meat products; and dairy products. Foods potentially contaminated with neural tissue (such as "mechanically separated meat," and meat cuts containing dorsal root ganglia or other neural tissue) are particularly important to screen for prion contamination.

Instruments that are used for invasive procedures may also be a source of transmitting disease. In one embodiment instruments used for medical and surgical procedures are tested for the presence of disease proteins using methods of the invention. In another embodiment instruments used for dental hygiene are tested for the presence of disease proteins.

In a further embodiment, the invention provides methods to ensure that decontamination methods for removing disease proteins and disease protein containing tissues, have been successful. In one embodiment the methods of the invention are used to assess decontamination procedures in a meat processing plant. In another embodiment the methods of the invention are used to assess decontamination in a food processing plant. In another embodiment instruments used for surgery or dentistry are tested for the presence of disease proteins.

The antibodies of the invention can be used in EPA. Thus, one aspect of the invention is a method of detecting whether a candidate polypeptide including a target epitope is in i) a wildtype conformation or ii) a non-wildtype conformation, wherein the candidate polypeptide is SOD1, and wherein the non-wildtype conformation is an aggregated form of SOD1, comprising:

contacting the polypeptide with a blocking agent that selectively blocks accessible target epitope, wherein in the wildtype conformation, the target epitope is accessible and reacts with the blocking agent, and wherein in the non-wildtype conformation, the target epitope is inaccessible and the target epitope cannot react with the blocking agent;

removing unreacted blocking agent from contact with the polypeptide;

modifying the candidate polypeptide to convert any inaccessible target epitope to accessible target epitope; and contacting the polypeptide with a detection agent that binds selectively to the target epitope that was converted from inaccessible target epitope to accessible target epitope, wherein binding between detection agent and converted target epitope indicates that the candidate polypeptide was in a non-wildtype conformation and wherein lack of binding between the detection agent and the target epitope indicates that the polypeptide was in a wild type conformation, and wherein the detection agent comprises an antibody specific for an ALS-specific epitope.

Another aspect of the invention is a method of detecting whether a candidate polypeptide including a target epitope, such as SOD1, is in i) a wildtype conformation or ii) a non-wildtype conformation, comprising:

contacting the polypeptide with a blocking agent that selectively blocks accessible target epitope, wherein in the non-wildtype conformation, the target epitope is accessible and reacts with the blocking agent, and wherein in the wildtype conformation, the target epitope is inaccessible and the target epitope cannot react with the blocking agent;

removing unreacted blocking agent from contact with the polypeptide;

modifying the candidate polypeptide to convert any inaccessible target epitope to accessible target epitope; and contacting the polypeptide with a detection agent that binds selectively to the target epitope that was converted from inaccessible target epitope to accessible target epitope, wherein binding between detection agent and converted target epitope indicates that the candidate polypeptide was in a wildtype conformation and wherein lack of binding between the detection agent and the target epitope indicates that the polypeptide was in a non-wildtype conformation, and wherein the detection agent comprises an antibody specific for a target epitope on SOD1 that is inaccessible to blocking agent.

Prognostic Applications

Prion protein conversion, Alzheimer's disease related polypeptide or other disease/disorder polypeptide may be periodically monitored in a subject over time (e.g. at a first time and a second time at least a week or at least a month after the first time) to identify, for example, increased or decreased levels of $PrP^C$ or increased or decreased levels of $PrP^{Sc}$ in the subject. The methods of the invention are also useful to measure a subject's level of $PrP^C$ or $PrP^{Sc}$ to determine the subject's response to drug therapy. Decreasing levels of prion protein in the subject over time indicate a positive response to drug therapy. The same methods are used with other disease or disorder protein.

Since many neurological diseases are associated with aggregated proteins, similar methods are useful for these diseases and their aggregated proteins, including, but not limited to: amyotrophic lateral sclerosis (superoxide dismutase 1), Alzheimer's disease (amyloid beta), Parkinson's disease (alpha synuclein), Huntington's disease (huntingtin), cancer (p53), diabetes (eg. islet amyloid polypeptide and resistin) and other diseases involving abnormal protein folding, aggregation or post-translational modification. Such a test is useful in the spinal fluid and other bodily fluids in addition to peripheral blood. In Alzheimer's disease, the aggregation status of the amyloid beta peptide is optionally monitored by determining the accessibility of two epitopes detected by the monoclonal antibodies 6E10 and 4G8, in addition to other amyloid beta epitopes, using the methods described in this application, for example, with an anti-6E10 or anti-4G8 antibody (detection agent) known in the art.

Identifying Prion Conversion Inhibitors

Since the invention is useful for detecting differences between polypeptides, the invention further includes an assay for evaluating whether a candidate compound is capable of inhibiting or stabilizing prion conversion or formation of other disease or disorder polypeptides, such as amyloid beta, tau and APP in Alzheimer's disease, SOD1 in amyotrophic lateral sclerosis, alpha-synuclein in Parkinson's and Lewy body disease, huntingtin in Huntington's disease islet amyloid polypeptide and resistin in diabetes and p53 in cancer. The invention also includes compounds for inhibiting or stabilizing prion conversion (or conversion of other disease or disorder polypeptides) identified by the methods described in the application. Decreased protein conversion to an intermediate prion protein substrate or $PrP^{Sc}$ (or other disease or disorder polypeptides shows that the candidate compound is useful for treating prion disease.

The assays of the invention are useful to screen candidate compounds to determine if they inhibit $PrP^{Sc}$ formation (or formation of other disease or disorder polypeptides from wild type protein). Protein may be contacted with a candidate compound in vivo or in vitro and then used in the methods of the invention to determine if wild type protein has been converted to $PrP^{Sc}$ or if $PrP^{Sc}$ has been converted to wild type protein. Similar methods are used with respect to other disease or disorder polypeptides. Recombinant proteins are useful for identifying aggregation inhibitors.

Therefore, the invention also provides methods for identifying substances that inhibit conversion to $PrP^{Sc}$ (e.g. prion protein conversion from wild type protein or intermediate to $PrP^{Sc}$) comprising the steps of:
reacting a polypeptide and a candidate substance, and
determining whether the protein has been converted to $PrP^{Sc}$ using the methods of the invention.

Similar methods are optionally performed to identify compounds which stabilize the wild-type prion state, or bind to $PrP^{Sc}$ and block conversion of recruitable PrP isoforms.

The invention also provides methods for identifying substances that inhibit conversion to disease or disorder polypeptides (e.g. conversion from wild type protein to the amyloid beta, tau or APP protein in Alzheimer's disease and other proteins and diseases described in this application) comprising the steps of:
reacting a polypeptide and a candidate substance, and
determining whether the protein has been converted to the amyloid betaor APP protein in Alzheimer's disease using the methods of the invention.

Another aspect of the invention provides a method of identifying substances which reverse $PrP^{Sc}$ formation comprising the steps of:
reacting a polypeptide and a candidate substance, and
determining whether the $PrP^{Sc}$ has been converted to wild type protein using the methods of the invention.

Another aspect of the invention provides a method of identifying substances which reverse amyloid beta or APP protein in Alzheimer's disease formation comprising the steps of:
reacting a polypeptide and a candidate substance; and
determining whether the amyloid beta or APP protein in Alzheimer's disease has been converted to wild type protein using the methods of the invention.

The same methods are used with other polypeptides associated with diseases and disorders described in this application.

Biological samples and commercially available libraries may be tested for substances such as proteins or small organic molecules that bind to a protein. Inhibitors are preferably directed towards specific domains of disease proteins such as prion protein. To achieve specificity, inhibitors should target the unique sequences and or conformational features of the disease protein.

Protein Conformation Detection

The invention includes a method of detecting whether a candidate polypeptide including a target epitope is a non-wild type conformation polypeptide or a wild type conformation polypeptide, comprising:
contacting the candidate polypeptide with a blocking agent; and
determining whether the target epitope is inaccessible or accessible to chemical modification by the blocking agent.

The accessibility or inaccessibility of the target epitope is indicative of whether the candidate polypeptide is non-wild type conformation polypeptide or a wild type conformation polypeptide because in one of the non-wild type protein and the wild type protein, the target epitope is accessible. In the other polypeptide, the target epitope is inaccessible.

In one embodiment, the invention includes a method of detecting whether a candidate polypeptide including a target epitope is in a wildtype conformation or a non-wildtype conformation, comprising:
contacting the polypeptide with a blocking agent that selectively blocks accessible target epitope, wherein in one of the non-wildtype conformation or the wildtype conformation, the target epitope is accessible and reacts with the blocking agent, and wherein in the other conformation, the target epitope is inaccessible and does not react with the blocking agent;
removing unreacted blocking agent from contact with the polypeptide (eg. by allowing blocking agent to be consumed or degraded in the sample comprising the candidate polypeptide or by physical or chemical removal processes);
modifying the candidate polypeptide to convert any inaccessible target epitope to accessible target epitope; and
contacting the polypeptide with a detection agent that binds selectively to target epitope that was converted from inaccessible target epitope to accessible target epitope, wherein binding between detection agent and converted target epitope indicates that prior to conversion the candidate polypeptide was in a conformation in which the target epitope was inaccessible and wherein lack of binding between the detection agent and the target epitope indicates that the polypeptide was in a conformation in which the target epitope was inaccessible, thereby indicating whether the polypeptide was in a wildtype conformation or a non-wildtype conformation.

A polypeptide may have more than two conformations. For example a polypeptide may exist in a wild-type conformation, in a benign misfolded, aggregated or otherwise non-wildtype conformation not associated with disease, and a disease associated conformation (i.e. aggregated in higher order structures). The methods of the invention can be applied to distinguish each of these states through the use of one or more chemical modifying agents and/or one or more detecting agents such as antibodies.

Detection of Intrinsically Modified Polypeptides

The invention also provides a method of detecting polypeptides that exist in two or more conformations wherein the target epitopes in one of the conformations is modified by an intrinsic mechanism. The intrinsic mechanism can include intracellular and/or post-translational modification of a polypeptide such as phosphorylation and/or glycosylation or a modification resulting from an additive used in a process. The intrinsic modification blocks a target epitope obscuring it from detection with a detection agent. The sample of polypeptide is reacted with a blocking agent that reacts with available target epitope in polypeptide that is not intrinsically modified. The intrinsic modification is then removed. For example if the intrinsic modification is phosphorylation, the polypeptide is treated with a phosphatase which removes the phosphorylation and converts the inaccessible target epitope in the previously intrinsically modified polypeptide, to accessible epitope. The polypeptide is then detected with a detecting agent such as an antibody.

Accordingly in one embodiment, the invention provides a method of detecting intrinsically modified target epitopes in a polypeptide having two or more conformations comprising;
  contacting the polypeptide with a blocking agent that selectively blocks accessible target epitope, wherein in one of the non-wildtype conformation or the wildtype conformation, the target epitope is accessible and reacts with the blocking agent, and wherein in the other conformation, the target epitope is inaccessible and does not react with the blocking agent;
  reacting the sample with an agent that removes the intrinsic modification from the intrinsically modified polypeptide target epitope;
  disaggregating and/or denaturing the polypeptide in the sample; and
  probing with a detection agent, such as antibodies against the target epitope, to determine whether the candidate polypeptide is an intrinsically modified polypeptide.

In one application, the methods of the invention can be used to detect whether polypeptides present in food items have been chemically modified by manufacturing processes. For example dairy products can be tested for the presence of formaldehyde, which is used as a bacteriostatic agent. Formaldehyde formylates gamma(2) casein (Pizzano R. et al J. Agric Food Chem (2004) 52:649-54) obscuring modified epitopes from subsequent detection by the detecting agent.

Kits

The methods described herein are optionally performed by utilizing pre-packaged diagnostic kits comprising the necessary reagents to perform any of the methods of the invention. For example, the kits typically include at least one specific nucleic acid, peptide or antibody described herein, which are conveniently used, e.g., in clinical settings, to screen and diagnose patients and to screen and identify those individuals expressing a disease conformation protein. Kit antibodies can comprise whole antibody, antibody fragments, single chain antibody, monoclonal antibody and/or polyclonal antibody. The kits optionally also include at least one chemical agent for modifying epitopes recognized by an antibody or aptamer. The kit is optionally based on ELISA technology such as sandwich ELISA and DELFIA and may employ detergents, precipitation agents (such as phosphotungstic acid) and adsorbents typically used in ELISA technology and known to one skilled in the art. The kit will also include detailed instructions for carrying out the methods of the invention. Recombinant protein are useful for standards in kits.

All such assays could be adapted and optimised to a simple high-throughput platform.

The following non-limiting examples are illustrative of the present invention.

EXAMPLES

Example 1

Figure 1:
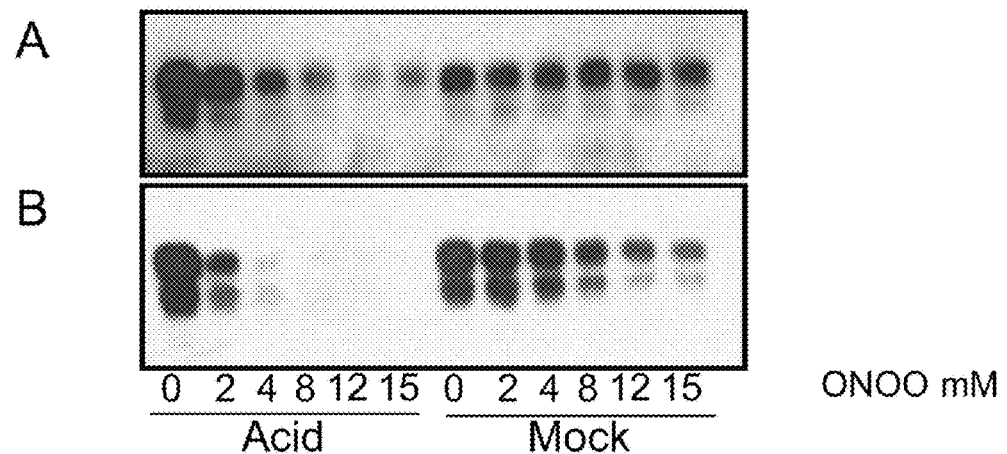
FIG. 1. Brain PrP aggregated in vitro by acid treatment is protected from modification by peroxynitrite Mock or acid treated human brain homogenate was treated with increasing concentrations of peroxynitrite (ONOO) and then subjected to immunoblotting with 3F4 (panel A) or 6H4 (panel B). Effect of peroxynitrite on the 3F4 (C) and 6H4 (D) epitope in mock (□) and acid treated (●) brain homogenate. Immunoblot films were scanned and band intensities determined by Unscanit software. The results are the combined relative intensities of 3 separate experiments.
Figure 1:
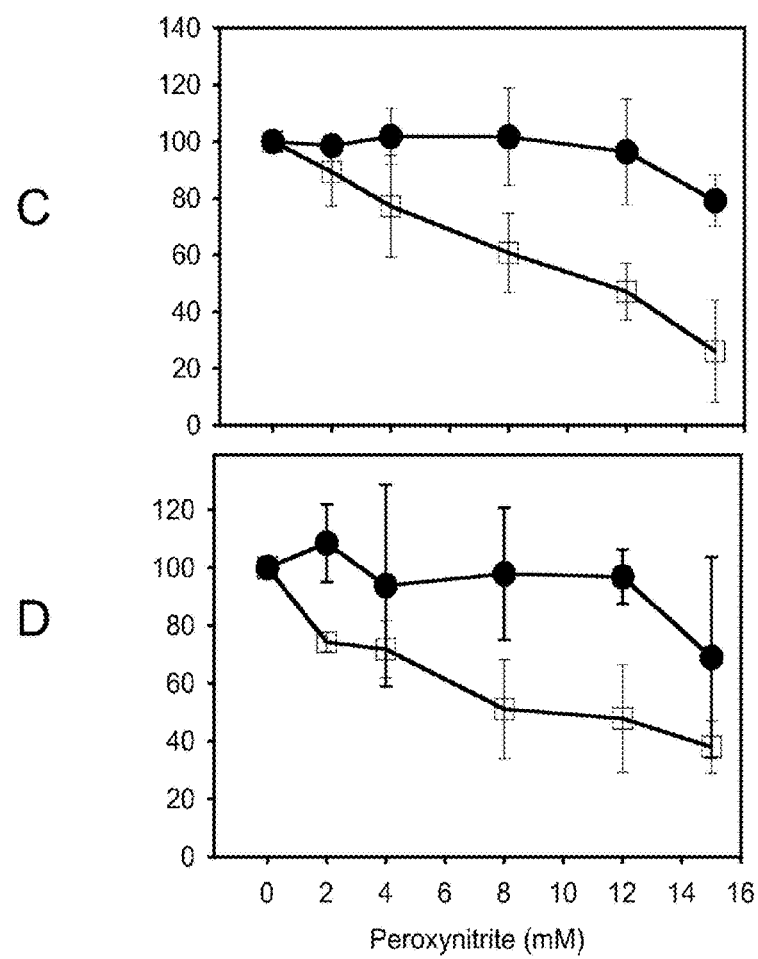

Peroxynitrite Reacts Differently with PrP in Normal and Acid Treated or Scrapie Brain Homogenate When brain homogenate is incubated at pH 3.5 in the presence of guanidine, PrP becomes detergent insoluble and is more susceptible to misfolding to a PK-resistant isoform in the presence of $PrP^{Sc}$ (29). This acid treated PrP is a 'model prion' which is partially misfolded and/or aggregated resembling characteristics of $PrP^{Sc}$. When mock (□) and acid treated (●) brain homogenate is incubated with increasing concentrations of peroxynitrite and then subjected to immunoblotting, there is less PrP recognized by both 3F4 (FIGS. 1A and C) and 6H4 (FIGS. 1B and D) in mock treated brain homogenate than in acid treated brain homogenate. The PrP in the acid treated brain homogenate is protected from modification by peroxynitrite.

Example 2

Figure 2:
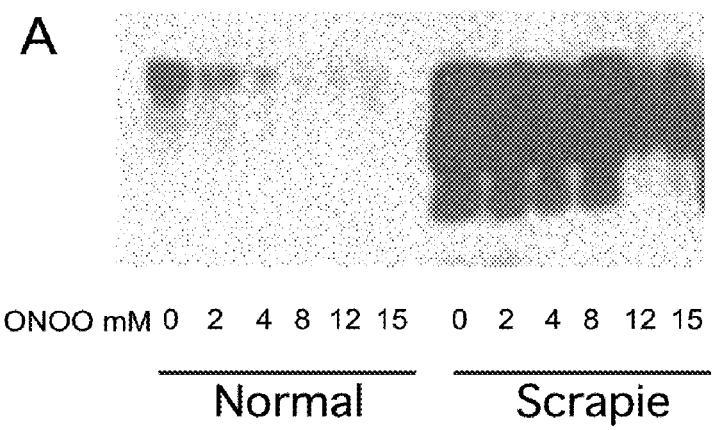
FIG. 2. PrP in scrapie infected hamster brain is protected from modification by peroxynitrite (A) Effect of peroxynitrite treatment on the 6H4 epitope in scrapie infected hamster brain. (B) The blot in (A) was scanned and relative band intensities determined using Unscanit software. (●) Scrapie infected hamster brain. (□) Normal hamster brain.
Figure 2:
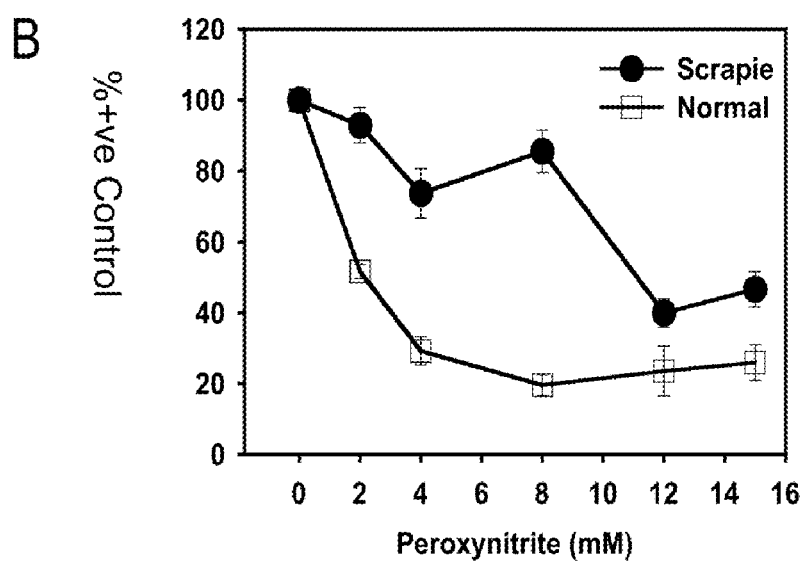

PrP in Scrapie Infected Hamster Brain is Protected from Modification by Peroxynitrite The epitope protection phenomenon for 'model prions' as observed in example 1 was also observed for authentic disease-misfolded prion protein in scrapie infected hamster (Ha) brain (FIGS. 2A and B). As with model prions, the 3F4 and 6H4 epitopes of PrP in $Ha^{Sc}$ brain homogenate are protected from modification by peroxynitrite. It is clear that 'model prions' and $HaPrP^{Sc}$ share characteristics that provide protection from chemical modification by peroxynitrite, such as differential misfolding or aggregation.

Example 3

Figure 3:
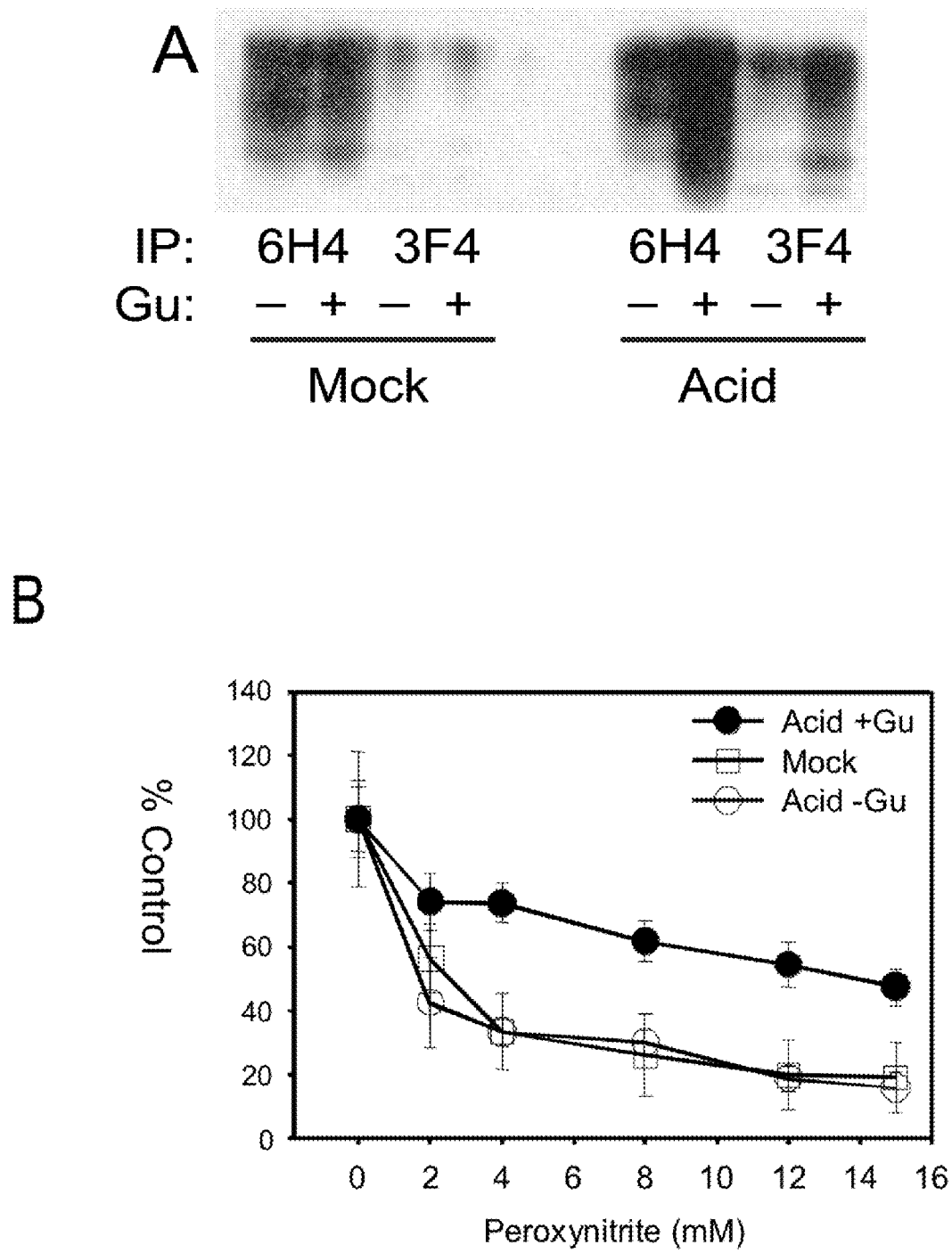
FIG. 3 Protection from peroxynitrite induced modification is due to aggregation in acid treated brain (A) Effect of peroxynitrite on the immunoprecipitation (IP) of PrP in mock and acid treated brain homogenate. Brain homogenate was treated with 10 mM peroxynitrite followed by incubation for 2 h at RT with (+) or without (−) 2.5 M guanidine hydrochloride (Gu). The resulting samples were immunoprecipitated with 6H4 or 3F4. More PrP is precipitated in the acid treated sample following treatment with peroxynitrite+Gu whereas in the mock sample, Gu has no effect. This suggests that Gu is able to break up aggregated PrP in the acid sample that is protected from destruction by peroxynitrite. (B) Effect of peroxynitrite on PrP in mock and acid treated brain homogenate as measured by ELISA. Brain homogenate was treated with increasing concentrations of peroxynitrite followed by 2.5 M Gu. Following a 10-fold dilution, the samples were analyzed by sandwich ELISA with 6H4 as the capture Ab and 3F4 as the detection Ab. Similar to the immunoblot and IP data, the results show that misfolded PrP is protected from destruction by peroxynitrite treatment, due to aggregation.

Aggregation is Responsible for the Reduction in Peroxynitrite-Induced Epitope Modification of Misfolded PrP To show that epitope protection of acid treated and scrapie brain was due to aggregation, samples were treated with peroxynitrite and then incubated with or without guanidine before immunoprecipitation. Treatment of the samples with guanidine dissociates aggregates of PrP (43-45) that protect the polypeptide from modification by peroxynitrite. Incubation of mock treated brain with 2.5 M guanidine after peroxynitrite treatment did not show an increase in 3F4 and 6H4 epitopes as revealed by immunoprecipitation (FIG. 3A lanes 1-4). However, when peroxynitrite-treated acid brain homogenate was incubated with guanidine, there was an increase in PrP that could be detected by immunoprecipitation with 3F4 and 6H4 immunobeads (FIG. 3A lanes 5-8). This shows that guanidine is able to dissociate aggregates of acid treated brain homogenate and release PrP that is protected from modification by peroxynitrite. Other means of solubilizing PrP aggregates were used and boiling samples in SDS loading buffer resulted in the greatest observed solubilization to date.

Example 4

Optimization of EPA Parameters

Titration experiments with peroxynitrite, hydrogen peroxide and methylene (based on UV light photolysis of the precursor diazirine) or other modifying agents, identify the optimal conditions for epitope protection in:

1. Normal hamster and human brain "model prions", using immunoblotting and conventional fluorescence ELISA.

2. Infectious prions from hamster and human brain, using immunoblotting analysis and time-resolved fluorescence In each case, brain homogenates are prepared and mixed with increasing concentrations of the modifying agent and processed as described (immunoblotting, and time resolved fluorescence). This defines the type and concentration of chemical agent allowing the maximal distinction between monomeric and aggregated prion proteins. Additional informative control experiments include using recombinant hamster $PrP^C$ in buffer and in $PrP^{-/-}$ knockout mouse brain, and by mouse normal and scrapie-infected brain (murine PrP is 6H4+ and 3F4−).

In some cases, infectious prions may have different properties for chemical modification than do "model prions," and brain prions may display different chemical modification properties than do endogenous prions circulating in blood, or $PrP^{Sc}$ detectable in urine of infected animals. One of skill in the art shall readily identify the optimal conditions for authentic endogenous prions using known techniques.

Example 5

EPA Adapted to a Fluorescent ELISA System

The epitope protection assay for aggregated PrP was adapted to a fluorescent sandwich ELISA system using 6H4 as the capture antibody and 3F4 as the detection antibody (FIG. 3B). The sandwich ELISA assay system is able to identify aggregated PrP in acid treated brain homogenate but only if the samples are boiled in SDS loading buffer after peroxynitrite treatment. At peroxynitrite concentrations greater than 8 mM, there is 2.5-3× as much PrP detected in the acid treated sample as compared to the mock treated sample.

Example 6

Detection of a Single Brain Prion

A single brain prion has been estimated to comprise $10^5$-$10^6$ molecules of $PrP^{Sc}$. Detection of $10^8$-$10^9$ molecules of recombinant PrP using conventional fluorescence ELISA has been accomplished. The assay used is about 1000-fold more sensitive for single-prion detection—the necessary sensitivity is provided by the Dissociation enhanced lanthanide fluoroimmunoassay (DELFIA). DELFIA uses a chelated lanthanide-labeled tracer, such as europium (Eu) and time-resolved fluorescence (TRF) to measure output signal. The benefit of lanthanide chelates is that their fluorescence duration is 200,000 times longer than conventional fluorophors, allowing signal capture after non-specific interfering fluorescence has faded (particularly critical for biological samples, which may possess considerable non-specific fluorescence). DELFIA-based systems can measure as little as 100 fmol/well of Eu which is >1000 times more sensitive than conventional ELISA assays, which detects single prions by EPA. The optimal TRF 96-well plate reader for the DELFIA system is manufactured by Wallac-Victor (Perkin-Elmer), and is used to automate sample analysis.

Using an optimal chemical modifier and optimal conditions a sensitive capture 96-well plate assay for detection of hamster and human prions, using the DELFIA TRF system is provided. This is used to:

1. Characterize, optimize and quantify detection of recombinant prion protein by TRF.
2. Determine the sensitivity of the DELFIA-TRF for hamster and human brain prions.

Example 7

Detection of Prion Proteins in Biological Fluids

The EPA achieves commercial utility by detecting $PrP^{Sc}$ in biological tissues and fluids for which no present technology exists. Blood prions are in very low abundance (10-100 prions/mL by bioassay, and protease-resistant PrP in urine is only intermittently/sporadically detectable by precipitation of large fluid volumes. Also, any prospective blood test must contend with high concentrations of $PrP^C$ ($10^6$-fold more than $PrP^{Sc}$) and "blocking" by heterologous plasma proteins. Using the optimized chemical modification regimen and the DELFIA-TRF system, the sensitivity thresholds for EPA in blood and urine are determined using:

1. Hamster and human plasma and urine "spiked" with a titration of 263K hamster prions;
2. Plasma and urine from Syrian hamsters "endogenously" infected with 263K prion disease Biological fluids clinically accessible by non-invasive routes provide a substrate for a practical antemortem test for diagnosis and screening of prion infection in humans and animals. The methods of this invention may also be used in post-mortem testing. One of skill in the art readily determines whether EPA with "prion spike" titration in normal blood and urine reveals similar DELFIA-TRF signals to the same prion titration in buffer, showing that the EPA is not affected by "blocking factors" in these biological fluids. Interestingly, preferential "blocking" of $PrP^{Sc}$ by heterologous proteins may actually enhance epitope protection to chemical modifying agents. If decreased detection of prions in blood or urine is observed, pre-clearing strategies are readily employed to enhance $PrP^{Sc}$ detection with detergents, precipitating agents, and adsorbents typically used in commercial ELISA assays which are known to one skilled in the art.

Human and bovine plasma and urine and other bodily fluids are tested using optimized EPA conditions and compared to samples from human variant CJD and BSE, respectively. Although the monoclonal antibody 6H4 recognizes PrP from all relevant species, other antibodies (commercially available) are used for the DELFIA TRF system for cattle, sheep, and cervids, which lack the 3F4 epitope. Other antibodies and epitopes useful in methods described in this application will be readily apparent to those of skill in the art.

Example 8

Detection of Aggregated Amyloid Beta (Abeta) Using EPA

Figure 4:
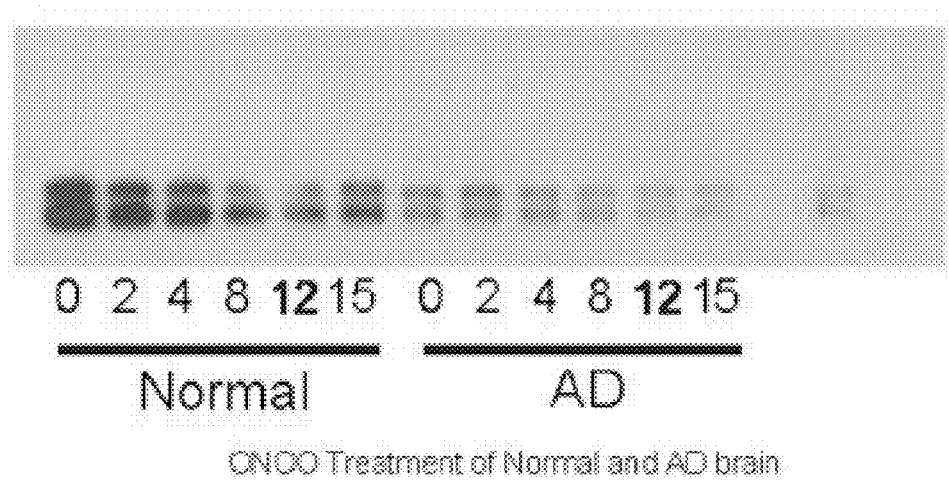
FIG. 4 Detection of aggregated amyloid beta (Abeta) using EPA
Figure 4:
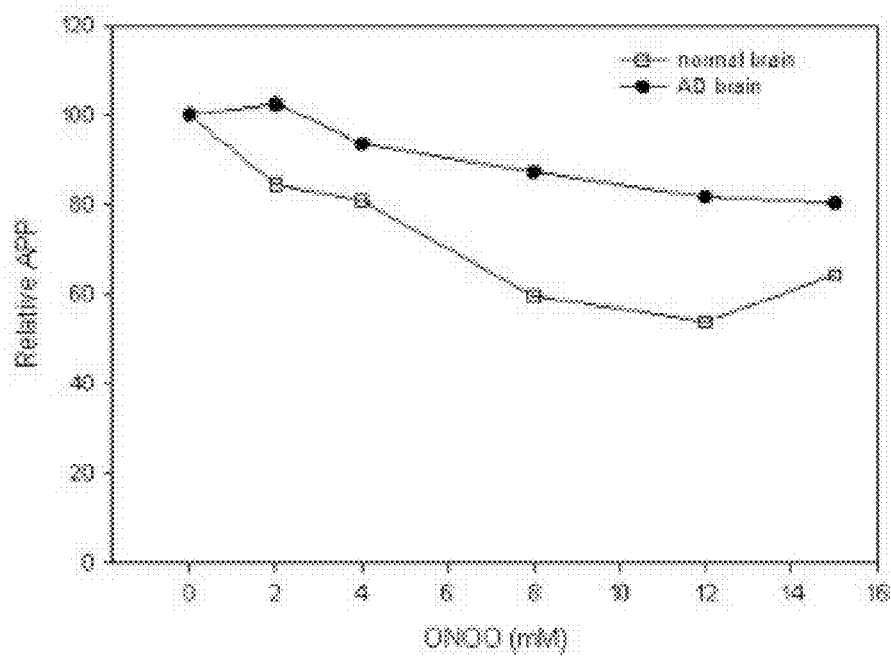

Amyloid beta peptide (Abeta) is a normal cleavage product of the proteolytic processing of amyloid precursor protein (APP). Abeta accumulates in discrete plaques in affected regions of Alzheimer's disease brain, and triggers neuronal death and gliosis observed in this disease. Plaque Abeta is aggregated and rich in beta-sheet structure, in contrast to the Abeta region of APP expressed by normal cells. Using epitope protection technology, it was demonstrated that the 6E10 epitope in the Abeta region of APP is less accessible to peroxynitrite modification in Alzheimer's disease brain compared to normal brain (FIG. 4 panel A). Similarly, the 6E10 epitope is partially protected in brain homogenates that have been treated at low pH to induce protein aggregation (FIG. 4 panel B). Abeta 1-42 peptide aggregated by overnight incubation at 1 mg/ml in water shows prominent epitope protection of the 6E10 epitope to peroxynitrite modification, in comparison with soluble non-aggregated Abeta 1-42 (FIG. 4 panel C). A further example of this phenomenon is presented in FIG. 4, panel D which shows normal (○) and aggregated (●) Abeta 1-42 treated with increasing concentrations of peroxynitrite, subjected to immunoblotting with 6E10 antibody.

The 6E10 epitope of APP is also unavailable to peroxynitrite modification in AD brain homogenates and in normal brain homogenates aggregated by low pH, but normal untreated brain does not show this protection (FIG. 4 panel A and B), showing molecular interaction in vivo of APP with an Abeta-domain blocking molecule (perhaps Abeta itself; ref. 9).

The sensitive and specific EPA detection of aggregated Abeta in biological fluids (such as blood and spinal fluid), or protection of Abeta epitopes in APP in cells and tissues, provides an antemortem diagnostic test for Alzheimer's disease. The methods of the invention described in this application are used for this diagnostic test.

Detection of Aggregated Tau Protein by EPA

Dying neurons release intracellular proteins such as tau into the CSF (39) and likely ultimately blood. Tau studies are directly performed on brain specimens including Alzheimer patient samples and control brain.

Example 9

Detection of Aggregated Superoxide Dismutase 1 (SOD1) by EPA

SOD1-containing cytoplasmic inclusions are detected in many diseased motor neurons from familial and sporadic ALS patients (15), and in most transgenic mouse (16, 17) and tissue culture models (18) of the disease. Human SOD1 can be aggregated in vitro. Further SOD1 is modifiable by succinic anhydride and DEPC. This property can be exploited by EPA technology to discriminate between aggregated and unaggregated SOD1 protein.

Purified SOD1 from human erythrocytes (Sigma) was aggregated in a metal-catalyzed oxidation reaction. Soluble SOD1 was treated with varying concentrations of DEPC, denatured with heat, and immunoblotted with anti-SOD1 antibodies. Western blotting shows that increasing concentrations of DEPC are associated with decreases in antibody binding in soluble SOD1 (FIG. 5) showing that sites are available for modification by a blocking agent.

Antibodies against SOD1 selected a priori for utility in EPA are used to distinguish disease specific aggregated SOD1 from wildtype SOD1. Relevant factors include:
1) selecting an epitope on the molecular surface of the native dimer to be accessible to chemical modification in the native soluble state;
2) identifying a linear epitope to optimize detection in the denatured state on immunoblots and ELISA;
3) immunogenicity;
4) uniqueness to SOD1; and
5) presence of acidic amino acids (Glu and Asp) that are readily modified by epoxides.

The five SOD1 sequences that meet these criteria are: 22QKESNG27 (SEQ ID NO:8); 51EDNTAGCTSA60 (SEQ ID NO:9); 74PKDEERHV81 (SEQ ID NO:10); 89ADKDG93 (SEQ ID NO:11); and 127GKG-GNEQSTK136 (SEQ ID NO:12) (in bold: solvated side chains).

Additionally the electrostatic loop sequence and zinc binding loop of human SOD1 are surface-accessible sequences and are involved in aggregate formation (Elan, J. et al. Nature Structural Biology (2003) 10:461-67).

These sequences are:

```
                                            (SEQ ID NO: 1)
Electrostatic loop of human SOD1:
Asp Leu Gly Lys Gly Gly Asn Glu Glu Ser Thr Lys Thr Gly Asn Ala Gly Ser (SEQ ID NO: 2)
Zinc-binding loop of human SOD1:
Asn Pro Leu Ser Arg Lys His Gly Gly Pro Lys Asp Glu Glu
```

Example 10

Detection of Aggregated Alpha-Synuclein by EPA

Most cases of Parkinson's disease are sporadic, but both sporadic and familial forms of the disease are characterized by intracellular Lewy bodies in dying neurons of the substantia nigra, a population of midbrain neurons (~60,000) that are selectively decimated in PD. Lewy bodies are predominantly composed of alpha-synuclein (22). Mutations in the gene encoding alpha-synuclein have been found in patients with familial Parkinson's disease (reviewed in 23). Another gene associated with autosomal recessive PD is parkin, which is involved in alpha-synuclein degradation (22, 23). Diffuse cortical Lewy bodies composed of alpha-synuclein are observed in Lewy body disease (LBD), a dementing syndrome associated with Parkinsonian tone changes, hallucinations, and rapid symptom fluctuation (24).

The Syn-1 epitope is optionally blocked by chemical modification of recombinant alpha-synuclein with DEPC (histidine reactive), and alpha-synuclein aggregated in vitro is partially protected from DEPC epitope blocking (FIG. 6).

Aggregated alpha-synuclein in vitro is protected from modification by DEPC whereas normal protein is not. Three mg/mL mutant A53T alpha-synuclein was incubated at 37° C. for three days for aggregation. The aggregation reaction was applied to ultracentrifugation. Normal protein prior to aggregation (containing soluble alpha-synuclein) and the pellet resuspension from the ultracentrifugation (containing insoluble alpha-synuclein) were treated with varying concentrations of DEPC, denatured with heat, and blotted with Syn-1 antibody from BD Biosciences. FIG. 6A shows that increasing concentrations of DEPC are associated with a gradual decrease in antibody binding in normal alpha-synuclein. Insoluble alpha-synuclein shows little change in antibody binding with increasing concentrations of DEPC until the DEPC concentrations reach 1 mM. A graphical representation of these findings is presented in FIG. 6B. The extent of antibody binding to DEPC-treated normal alpha-synuclein (■) decreases gradually overall but more rapidly at higher concentrations of DEPC. Insoluble alpha-synuclein (▲), on the other hand, shows little change in the extent of antibody binding. The last data point at 0.01M DEPC for insoluble alpha-synuclein increases due to the darkening of the film.

Example 11

Detection of Aggregated Proteins in CSF

Extracellularly deposited Abeta has been quantified in CSF and blood of patients with AD and normal controls (6-8). Intracellular neuronal proteins, such as alpha-synuclein, have been detected in CSF and blood (37, 38). Dying neurons release intracellular proteins 14-3-3, neuron-specific enolase, tau, and alpha-synuclein into the CSF (39), and likely ultimately blood. A proportion of released protein in disease is in an aggregated form. EPA technology is applied to determine the proportion of polypeptide aggregates in CSF samples from patients with AD, ALS, PD, and LBD. Signal is measured for polypeptides disaggregated before and after chemical treatment, representing "total" and "protected" epitopes, respectively, to determine the proportion of polypeptide in the aggregated state. Using the optimized mAbs and chemical modification regimens, and the DELFIA-TRF system, EPA sensitivity is determined in:
1. Normal CSF "spiked" with polypeptides aggregated in vitro.
2. CSF from patients with AD, ALS, PD, and LBD.

The proportion of aggregated polypeptides in a CSF sample, is determined even if it constitutes only $10^5$-$10^6$ molecules. Detergents, precipitating agents (such as phosphotungstic acid), and adsorbents typically used in commercial ELISA assays to enrich for relevant species are optionally employed. Biological fluids clinically accessible by non-invasive routes provides an ideal substrate for a practical antemortem test for diagnosis and screening of neurodegenerative diseases.

Materials and Methods

Materials

Recombinant hamster PrP (rhaPrP) and 6H4 was from Prionics. Recombinant human PrP (rhuPrP) was from Roboscreen. Biotin-3F4 and 3F4 were from Signet. 3F4 reacts against MKHV and 6H4 reacts against DYEDRYYRE. 6E10 anti-Abeta (from Signet) reacts against EFRHDS (residues 3-8).

Other antibodies and the epitopes recognized if known, are provided in table 1 above.

Preparation of Acid-Misfolded PrP and APP

Acid misfolded PrP was used as "model prions" in this study and was prepared as in (29). Briefly, 100 μl of 10% brain homogenate was mixed with an equal volume of 3.0 M Gdn-HCl (final concentration 1.5 M) in PBS at pH 7.4 or pH 3.5 adjusted with 1 N HCl, followed by rotation at room temperature. After 5 h incubation, samples were methanol precipitated with 5 volumes of ice-cold methanol and pellets were resuspended in 100 μl of lysis buffer. The samples treated at pH 7.4 were designated as mock-treated samples.

Peroxynitrite Treatment of Brain Homogenates

An aliquot (18 μl) of normal or misfolded/diseased brain homogenate was vortexed while 2 μl of peroxynitrite in 100 mM NaOH/60 mM $H_2O_2$ was added to give a final peroxynitrite concentration of 0-15 mM. After vortexing for a further 15 s, the samples were subjected to Western blotting, immunoprecipitation or sandwich ELISA.

DEPC Treatment of Erythrocyte SOD1

Purified SOD1 from human erythrocytes (Sigma) is aggregated in a metal-catalyzed oxidation reaction consisting of 40 μM SOD1, 4 mM ascorbic acid, and 0.2 mM $CuCl_2$ in 10 mM Tris-acetate buffer (pH7) at 37° C. for three days. Ultracentrifuged supernatant (containing soluble SOD1) and the pellet resuspension (containing insoluble SOD1) are treated with varying concentrations of DEPC (100 μM to 0.1 M), denatured with heat, and immunoblotted with anti-SOD1.

Western Blotting

Samples were boiled in SDS loading buffer (62 mM Tris (pH 6.8), 10% glycerol, 2% SDS, 5% beta-mercaptoethanol and 0.01% bromphenol blue) for 5 min. and separated on 12% Tris-Glycine polyacrylamide gels followed by transfer to Hybond-P. PrP was detected using 3F4 (1:50000) 6H4 (1:10000) or 6E10 (1:1000) as the primary antibodies and HRP-conjugated goat anti-mouse (1:10000) as the secondary antibody followed by exposure to ECL-Plus and visualization by exposure to Kodak X-OMAT film. Band intensities were quantitated using UnScan-IT software.

Immunoprecipitation

Samples were incubated with 50 μl of Ab-conjugated (100 μg/ml) Dynal M-280 magnetic beads in a final volume of 1 ml binding buffer (3% NP-40; 3% Tween-20) for 3 h at room temperature with rotation. Beads were washed in wash buffer (2% NP-40; 2% Tween-20)×3 and boiled in 30 μl SDS loading buffer without beta-mercaptoethanol for 5 min. Supernatants were analyzed by Western blotting as described above.

Sandwich ELISA

The capture antibody (6H4; 1:5000 in 50 mM bicarbonate binding buffer, pH 9.6) was bound to an opaque 96-well plate (Nunc Maxisorp) by overnight incubation at 4° C. After blocking with 1% BSA in 0.05% TBST for 2 h, plates were washed 3× in TBST and incubated overnight at 4° C. with standard concentrations of rhuPrP or rHaPrP along with unknown brain homogenates. Plates were washed 3× and incubated with the detecting antibody biotin-3F4 (1:5000) at RT for 1 h. After washing 3×, avidin-HRP (1:5000) was added and incubated for 30 min. at RT. Following a final wash step (×3) the plate was developed with Quantablu fluorescent substrate for 10-90 min at RT and fluorescent intensities determined with an excitation of 325 nm and emission of 420 nm.

Example 12

Antibody Production

An ALS-specific epitope (DLGKGGNEESTKTGNAGS) bearing an N-terminal Cys residue was conjugated to KLH for immunization of Balb/c mice, and BSA for ELISA screening. Multiple immune injections were done for each projects at 21-day internal. The adjuvant for first injection was Complete Freund's Adjuvant (Sigma, Cat# F5881-6×10 mL), and Incomplete Freund's Adjuvant (Sigma, Cat# F5506-6×10 mL) for the rest of the boosts. The test bleeds were collected at day 7-10 after the 3rd injection. The cell fusion was done 3-4 days later after the final boost without any adjuvant.

The fusion partner used was Sp 2/0-Ag14 (ATCC# CRL-1581). The fusion between fusion partner SP2/0 and spleen cells was done at 1:5 ratio ($2.0 \times 10^7$: $1.0 \times 10^8$) and 1 ml pre-warmed PEG (MW1450: Sigma, Cat# P7181) was added. Fusion cells were re-suspended into 50 ml of DMEM with 10% FBS and plated into 5 96-well plates at 100 μl/well. 100 μl/well of 2×HAT DMEM medium was added after fusion cells growing in normal medium for 24 hours. Medium was changed on day 5 and 7 with fresh 1×HAT medium. On day 10-12, 50 μl of supernatant was picked from each well for first ELISA screening. Cherry-picking on same day, positive clones were transferred to 24 well plates. Antibody supernatants were screened by ELISA with both specific antigen and non-related antigen upon cells confluence in 24-well plates. Positive clones were transferred to 6-well plates for expansion or subcloning. The subcloning was done by limiting dilution at 50-70 cells/96-well plate.

For large scale antibody production, 0.2-0.5 ml of Pristane (Sigma, Cat#T-7640) or IFA was injected to each mouse (Balb/c) by i.p. for priming. On day 7-14, 500,000 to 5,000,000 hybridoma cells in 0.5 ml 1×PBS at log phase were injected to each mouse by i.p. The ascitic fluid was build up within 1-2 weeks. 2-5 ml of ascites can be tapped from each mouse, and the IgG concentration around 1-9 mg/ml. Protein A was used to do the IgG2 and 3 purification, and Protein G for IgG1.

The IgG mAb clone was designated 10E11C11. This antibody displays properties consistent with its recognition of a disease-specific epitope for monomeric or misfolded SOD1. This mAb binds to denatured SOD1 on immunoblot membranes, recognizing monomeric denatured SOD1 (unstructured). The mAb does not recognize the dimeric SOD1 on immunoblotting. On immunoprecipitations mediated by 10E11EC11 conjugated magnetic beads, there is no detectable binding of native SOD1 from normal human brain or mouse brain and spinal cord. The mAb does efficiently immunoprecipitate SOD1 deliberately misfolded by low pH, the chaotrope guanidine, or both. Most importantly, 10E11C11 efficiently immunoprecipitates misfolded SOD1 in a mouse model of ALS caused by transgenic overexpression of mutant SOD1 (G93A). Notably, mouse endogenous SOD1 present in the same tissue is not immunoprecipitated, suggesting that the misfolded human mutant SOD1 does not "co-recruit" normal mouse SOD in this disease model.

Antibodies were also raised in a like manner to the epitope NPLSRKHGGPKDEE, bearing an N-terminal Cys residue.

The antibodies are readily available and can be obtained from Neil Cashman at the Brain Research Centre, UBC Hospital, 2211 Wesbrook Mall, Vancouver, British Columbia, V6T 2B5, Canada (neil.cashman@utoronto.ca).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications, including U.S. application No. 60/496,381 (entitled Methods of Detecting Prion Protein (Cashman & Lehto), filed on Aug. 20, 2003 and U.S. application No. 60/497,362 (entitled Epitope Protection Assay (Cashman & Lehto), filed on Aug. 21, 2003 and the Corresponding Canadian applications nos. 2,437,675 and 2,437,999 are herein incorporated by reference in their entirety to the same extent as if each individual publication, patent or patent application was specifically and individually indicated to be incorporated by reference in its entirety.

REFERENCES

1. Prusiner S B. Shattuck lecture—neurodegenerative diseases and prions. N Engl J. Med. 344:1516-26, 2001.
2. Caselli R J. Current issues in the diagnosis and management of dementia. Semin Neurol. 23:231-40, 2003.
3. Cashman N R. Do the benefits of currently available treatments justify early diagnosis and announcement? Arguments for. Neurology. 53(Suppl 5):S50-2, 1999.
4. Selkoe D J. Alzheimer's disease: genes, proteins, and therapy. Physiol Rev. 81:741-66, 2001.
5. Puglielli L, Tanzi R E, Kovacs D M. Alzheimer's disease: the cholesterol connection. Nat. Neurosci. 6:345-51, 2003.
6. Mehta P D, Pirttila T, Mehta S P. Plasma and cerebrospinal fluid levels of amyloid beta proteins 1-40 and 1-42 in Alzheimer disease. Arch Neurol. 57:100-5, 2000.
7. Clark C M, Xie S, Chittams J et al. Cerebrospinal fluid tau and beta-amyloid: how well do these biomarkers reflect autopsy-confirmed dementia diagnoses? Arch Neurol. 60:1696-702, 2003.
8. Green A J. Cerebrospinal fluid brain-derived proteins in the diagnosis of Alzheimer's disease and Creutzfeldt-Jakob disease. Neuropathol Appl Neurobiol. 28:427-40, 2002.
9. Lorenzo A, Yuan M, Zhang Z, et al. Amyloid beta interacts with the amyloid precursor protein: a potential toxic mechanism in Alzheimer's disease. Nat. Neurosci. 3:460-4, 2000.
10. Rosen D R, Siddique T, Patterson D. et al. Mutations in Cu/Zn superoxide dismutase gene are associated with familial amyotrophic lateral sclerosis. Nature. 362:59-62, 1993.
11. Deng H X, Hentati A, Tainer J A et al. Amyotrophic lateral sclerosis and structural defects in Cu,Zn superoxide dismutase. Science. 20; 261:1047-51, 1993.
12. Anderson, P M in Brown R H, Meininger V, Swash eds. Amyotrophic Lateral Sclerosis. London: Martin Dunitz. 2000.
13. Gumey, M. E., Pu, H., Chiu, A. Y., et al. Motor neuron degeneration in mice that express a human Cu,Zn superoxide dismutase mutation. Science 264:1772-1775, 1994.
14. Ripps, M. E., Huntley, G. W., Hof, P. R., et al. Transgenic mice expressing an altered murine superoxide dismutase gene provide an animal model of amyotrophic lateral sclerosis. Proc. Natl. Acad. Sci. U.S.A 92: 689-693, 1995.
15. Kato, S., Takikawa, M., Nakashima, K., et al. New consensus research on neuropathological aspects of familial amyotrophic lateral sclerosis with superoxide dismutase 1 (SOD1) gene mutations: inclusions containing SOD1 in neurons and astrocytes. Amyotroph. Lateral. Scler. Other Motor Neuron Disord. 1: 163-184, 2000.
16. Bruijn, L. I., Becher, M. W., Lee, M. K. ALS-linked SOD1 mutant G85R mediates damage to astrocytes and promotes rapidly progressive disease with SOD1-containing inclusions. Neuron 18: 327-338, 1997.
17. Bruijn, L. I., Houseweart, M. K., Kato, S., Aggregation and motor neuron toxicity of an ALS-linked SOD1 mutant independent from wild-type SOD1. Science 281: 1851-1854, 1998.

18. Durham, H. D., Roy, J., Dong, L., and Figlewicz, D. A. Aggregation of mutant Cu/Zn superoxide dismutase proteins in a culture model of ALS. J. Neuropathol. Exp. Neurol. 56:523-530, 1997.
19 Li Y K, Chir J, Chen F Y. Catalytic mechanism of a family 3 beta-glucosidase and mutagenesis study on residue Asp-247. Biochem J 355(Pt 3):835-40, 2001
20 Rose R B, Rose J R, Salto R, Craik C S, Stroud R M. Structure of the protease from simian immunodeficiency virus: complex with an irreversible nonpeptide inhibitor. Biochemistry 32:12498-507, 1993.
21. Olanow C W. The scientific basis for the current treatment of Parkinson's disease. Annu Rev Med 55:41-60, 2004.
22. Iwatsubo T. Aggregation of alpha-synuclein in the pathogenesis of Parkinson's disease. Neurol 250 Suppl 3:III11-4, 2003.
23. Eriksen J L, Dawson T M, Dickson D W, Petrucelli L Caught in the ac: alpha-synuclein is the culprit in Parkinson's disease. Neuron 40:453-6, 2003.
24. McKeith I, Mintzer J, Aarsland D et al. Dementia with Lewy bodies. Lancet Neurol 3:19-28, 2004.
25 Alvarez B, Ferrer-Sueta G, Freeman B A, Radi R. Kinetics of peroxynitrite reaction with amino acids and human serum albumin. J Biol Chem 274:842-8, 1999.
26. Alvarez B, Radi R Peroxynitrite reactivity with amino acids and proteins. Amino Acids 25:295-311, 2003.
27. Sokol P P, Holohan P D, Ross C R. Arginyl and histidyl groups are essential for organic anion exchange in renal brush-border membrane vesicles. J Biol Chem 263:7118-23, 1988.
28. Zou W-Q, Yang D-S, Fraser P E, Cashman N R, Chakrabartty A. All-or-none fibrillogenesis of a prion peptide. Europ J Biochem 268:4885-4891, 2001.
29. Zou W-Q, Cashman N R. Acidic pH and detergents enhance in vitro conversion of human brain PrPC to a PrPSc-like form. J Biol Chem 277:43942-43947 2002.
30. Rakhit R, Cunningham P, Furtos-Matei A, Dahan S, Qi X-F, Crow J, Cashman N R, Kondejewski L H, Chakrabartty A. Oxidation-induced misfolding and aggregation of superoxide dismutase and its implications for amyotrophic lateral sclerosis. J Biol Chem 277:47551-6 2002, 2002.
31. Paramithiotis E, Pinard M, Lawton T, LaBoissiere S, Leathers V L, Zou W-Q, Estey L A., Kondejewski L H, Francoeur G P, Papadopoulos M, Haghighat A, Spatz S J, Tonelli Q, Ledebur H C, Chakrabartty A, Cashman N R. A PrPSc-specific immunological epitope. Nature Medicine 9:893-9, 2003.
32. Rakhit R, Crow J P, Lepock J R, Kondejewski L H, Cashman N R, Chakrabartty A. Monomeric Cu/Zn superoxide dismutase is a common misfolding intermediate in the oxidation models of sporadic and familial ALS. J Biol Chem e-pub January 2004.
33. MacGregor, I., Hope, J., Barnard, G. Application of a time-resolved fluoroimmunoassay for the analysis of normal prion protein in human blood and its components. Vox Sang 77:88-96, 1999.
34. Chishti M A, Yang D S, Janus C et al. Early-onset amyloid deposition and cognitive deficits in transgenic mice expressing a double mutant form of amyloid precursor protein 695. J Biol Chem 276:21562-70, 2001.
35. Bolton D. C., McKinley M. P., and Prusiner S. B. Identification of a protein that purifies with the scrapie prion. Science 218:1309-1311, 1982.
36. Beekes M., Baldauf E., and Diringer H. Sequential appearance and accumulation of pathognomic markers in the central nervous system of hamsters orally infected with scrapie J. Gen. Virol 77:1925-1934, 1996.
37. Borghi R, Marchese R, Negro A, et al. Full length alpha-synuclein is present in cerebrospinal fluid from Parkinson's disease and normal subjects. Neurosci Lett. 287:65-7, 2000.
38. El-Agnaf O M, Salem S A, Paleologou K E, et al. Alpha-synuclein implicated in Parkinson's disease is present in extracellular biological fluids, including human plasma. FASEB J 17:1945-7, 2003.
39. Verbeek M M, De Jong D, Kremer H P. Brain-specific proteins in cerebrospinal fluid for the diagnosis of neurodegenerative diseases. Ann Clin Biochem 40(Pt 1):25-40, 2003.
40. Coulthart, M. B. and Cashman, N. R. (2001) *CMAJ* 165, 51-58
41. Prusiner, S. B. (1998) *Proc. Natl. Acad. Sci. U.S.A* 95, 13363-13383
42 Will, R. G., Ironside, J. W., Zeidler, M., Cousens, S, N., Estibeiro, K., Alperovitch, A., Poser, S., Pocchiari, M., Hofman, A., and Smith, P. G. (1996) *Lancet* 347, 921-925.
43. Kocisko, D. A., Lansbury, P. T., Jr., and Caughey, B. (1996) *Biochemistry* 35, 13434-13442
44, Barnard, G., Helmick, B., Madden, S., Gilbourne, C., and Patel, R. (2000) *Luminescence*. 15, 357-362
45. Meyer, R. K., Oesch, B., Fatzer, R., Zurbriggen, A., and Vandevelde, M. (1999) *J. Virol.* 73, 9386-9392
46. Kang, S. C., Li, R., Wang, C., Pan, T., Liu, T., Rubenstein, R., Barnard, G., Wong, B. S., and Sy, M. S. (2003) *J. Pathol.* 199, 534-541.
47. Shaked G M, Shaked Y, Kariv-Inbal Z, Halimi M, Avraham I, Gabizon R. (2001) J Biol. Chem. 276, 31479-82.
48. Ross C A et al. Nature Medicine, (2004) S10-17.)
49. Davies S W et al Cell 90, 537-548 (1997).
50. Scherzinger E et al. Proc. Natl. Acad. Sci. USA 96, 4604-9, (1999).
51. Sen S et al Protein Sci. (2003) 12:953-962.
52. Llewelyn C A et al. Lancet (2004) 363:417-421.
53. Peden A H et al. Lancet (2004) 364:527-529.
54. Andreoletti O et al. Nat. Med. (2004) 6:591-593.
55. Thomzig A et al. J Clin Invest. (2004) 10:1465-72.
56 Glatzel M et al. N Engl J. Med. (2003) 349:1812-20.
57 Bosque P J et al. Proc Natl Acad Sci USA. (2002) 99:3812-7.

I claim:

1. A composition for eliciting an immune response in an animal to produce an antibody that binds selectively to an amyotrophic lateral sclerosis (ALS)-specific epitope, the composition comprising an effective amount of the isolated ALS-specific epitope in admixture with a suitable diluent or carrier, wherein the ALS-specific epitope is an isolated peptide consisting of the amino acid sequence NPLSRKHGGP-KDEE (SEQ ID NO:2).

2. The composition of claim 1, further comprising an adjuvant.

3. The composition of claim 2, wherein the epitope is conjugated to a molecule that enhances immunogenicity of the epitope.

4. The composition of claim 3, wherein the molecule comprises keyhole limpet hemocyanin.

* * * * *

SEQUENCE LISTING

<160> NUMBER OF SEQ ID NOS: 12

<210> SEQ ID NO 1
<211> LENGTH: 18
<212> TYPE: PRT

-continued

```
<213> ORGANISM: Homo sapiens

<400> SEQUENCE: 1

Asp Leu Gly Lys Gly Gly Asn Glu Glu Ser Thr Lys Thr Gly Asn Ala
1               5                   10                  15

Gly Ser

<210> SEQ ID NO 2
<211> LENGTH: 14
<212> TYPE: PRT
<213> ORGANISM: Homo sapiens

<400> SEQUENCE: 2

Asn Pro Leu Ser Arg Lys His Gly Gly Pro Lys Asp Glu Glu
1               5                   10

<210> SEQ ID NO 3
<211> LENGTH: 4
<212> TYPE: PRT
<213> ORGANISM: Artificial sequence
<220> FEATURE:
<223> OTHER INFORMATION: epitope

<400> SEQUENCE: 3

Met Lys His Val
1

<210> SEQ ID NO 4
<211> LENGTH: 9
<212> TYPE: PRT
<213> ORGANISM: Artificial sequence
<220> FEATURE:
<223> OTHER INFORMATION: epitope

<400> SEQUENCE: 4

Asp Tyr Glu Asp Arg Tyr Tyr Arg Glu
1               5

<210> SEQ ID NO 5
<211> LENGTH: 6
<212> TYPE: PRT
<213> ORGANISM: Artificial sequence
<220> FEATURE:
<223> OTHER INFORMATION: epitope

<400> SEQUENCE: 5

Glu Phe Arg His Asp Ser
1               5

<210> SEQ ID NO 6
<211> LENGTH: 54
<212> TYPE: RNA
<213> ORGANISM: Homo sapiens

<400> SEQUENCE: 6
gauuuaggua aggugguaa ugaagaaagu acuaaaacug guaaugcugg uagu            54

<210> SEQ ID NO 7
<211> LENGTH: 42
<212> TYPE: RNA
<213> ORGANISM: Homo sapiens

<400> SEQUENCE: 7
aauccuuuaa gucguaaaca cggaggaccg aaggacgagg ag                        42
```

```
<210> SEQ ID NO 8
<211> LENGTH: 6
<212> TYPE: PRT
<213> ORGANISM: Homo sapiens

<400> SEQUENCE: 8

Gln Lys Glu Ser Asn Gly
1               5

<210> SEQ ID NO 9
<211> LENGTH: 10
<212> TYPE: PRT
<213> ORGANISM: Homo sapiens

<400> SEQUENCE: 9

Glu Asp Asn Thr Ala Gly Cys Thr Ser Ala
1               5                   10

<210> SEQ ID NO 10
<211> LENGTH: 8
<212> TYPE: PRT
<213> ORGANISM: Homo sapiens

<400> SEQUENCE: 10

Pro Lys Asp Glu Glu Arg His Val
1               5

<210> SEQ ID NO 11
<211> LENGTH: 5
<212> TYPE: PRT
<213> ORGANISM: Homo sapiens

<400> SEQUENCE: 11

Ala Asp Lys Asp Gly
1               5

<210> SEQ ID NO 12
<211> LENGTH: 10
<212> TYPE: PRT
<213> ORGANISM: Homo sapiens

<400> SEQUENCE: 12

Gly Lys Gly Gly Asn Glu Gln Ser Thr Lys
1               5                   10
```